United States Patent
Prud'homme et al.

(10) Patent No.: US 12,186,436 B2
(45) Date of Patent: Jan. 7, 2025

(54) TRIBLOCK COPOLYMER STABILIZERS FOR THE FORMATION OF NANOPARTICLES ENCAPSULATING SOLUBLE BIOLOGICS, THERAPEUTICS, AND IMAGING AGENTS

(71) Applicant: The Trustees of Princeton University, Princeton, NJ (US)

(72) Inventors: Robert K. Prud'homme, Princeton, NJ (US); Chester E. Markwalter, Princeton, NJ (US); Robert F. Pagels, Princeton, NJ (US)

(73) Assignee: The Trustees of Princeton University, Princeton, NJ (US)

(*) Notice: Subject to any disclaimer, the term of this patent is extended or adjusted under 35 U.S.C. 154(b) by 686 days.

(21) Appl. No.: 17/260,640

(22) PCT Filed: Jul. 19, 2019

(86) PCT No.: PCT/US2019/042574
§ 371 (c)(1),
(2) Date: Jan. 15, 2021

(87) PCT Pub. No.: WO2020/018890
PCT Pub. Date: Jan. 20, 2020

(65) Prior Publication Data
US 2021/0259984 A1    Aug. 26, 2021

Related U.S. Application Data

(60) Provisional application No. 62/700,854, filed on Jul. 19, 2018.

(51) Int. Cl.
*A61K 9/51* (2006.01)
*C08G 63/08* (2006.01)
*C08G 63/664* (2006.01)
*C08G 73/10* (2006.01)
*C08G 81/00* (2006.01)
*B82Y 5/00* (2011.01)
*B82Y 30/00* (2011.01)
*B82Y 40/00* (2011.01)

(52) U.S. Cl.
CPC .......... *A61K 9/5192* (2013.01); *A61K 9/5153* (2013.01); *A61K 9/5169* (2013.01); *C08G 63/08* (2013.01); *C08G 63/664* (2013.01); *C08G 73/1092* (2013.01); *C08G 81/00* (2013.01); *B82Y 5/00* (2013.01); *B82Y 30/00* (2013.01); *B82Y 40/00* (2013.01)

(58) Field of Classification Search
CPC .. A61K 9/5192; A61K 9/5153; A61K 9/5169; C08G 63/08; C08G 63/664; C08G 73/1092; C08G 81/00; C08G 63/6852; B82Y 5/00; B82Y 30/00; B82Y 40/00; C12N 15/88

USPC .......................................................... 424/497
See application file for complete search history.

(56) References Cited

U.S. PATENT DOCUMENTS

| | | | |
|---|---|---|---|
| 1,690,760 | A | 11/1928 | Volwiler |
| 4,342,653 | A | 8/1982 | Halverson |
| 4,382,982 | A | 5/1983 | Whillans |
| 4,678,516 | A | 7/1987 | Alderman |
| 4,695,464 | A | 9/1987 | Alderman |
| 4,888,238 | A | 12/1989 | Katz et al. |
| 4,999,417 | A | 3/1991 | Domb |
| 5,366,734 | A | 11/1994 | Hutchinson |
| 5,578,325 | A | 11/1996 | Domb et al. |
| 5,851,579 | A | 12/1998 | Wu |
| 6,291,013 | B1 | 9/2001 | Gibson |
| 6,383,500 | B1 | 5/2002 | Wooley et al. |
| 6,610,653 | B1 | 8/2003 | Backstrom et al. |
| 6,730,322 | B1 | 5/2004 | Bernstein et al. |

(Continued)

FOREIGN PATENT DOCUMENTS

| | | |
|---|---|---|
| CN | 100389766 C | 5/2008 |
| CN | 102334609 A | 2/2012 |

(Continued)

OTHER PUBLICATIONS

Kader A. and Jalil R. In Vitro Release of Theophylline from Poly(Lactic Acid) Sustained-Release Pellets. Prepared by Direct Compression. Drug Development and Industrial Pharmacy, 24(6), 527-534 (1998) (Year: 1998).*
Lan Q et al. Preparation and Characterization of Super Cross-Linked Poly(ethylene oxide) Gel Polymer Electrolyte for Lithium-Ion Battery. Science of Advanced Materials, vol. 9, No. 6, Jun. 2017, pp. 988-994(7) (Year: 2017).*
International Patent Application PCT/US2018/050714 International Search Report and Written Opinion dated Dec. 6, 2018.
International Patent Application PCT/US2018/058869 International Search Report and Written Opinion dated Feb. 22, 2019.
International Patent Application PCT/US2019/042574 International Search Report and Written Opinion dated Nov. 22, 2019.

(Continued)

*Primary Examiner* — Jessica Worsham
*Assistant Examiner* — Ngoc-Anh Thi Nguyen
(74) *Attorney, Agent, or Firm* — Nixon & Vanderhye P.C.; Lars H. Genieser

(57) ABSTRACT

Hydrophilic molecules such as biologics, which can include peptides, proteins, and other biologically-derived materials, can be used as therapeutic agents in medical applications. They can face administration challenges because of poor membrane permeability and rapid clearance from the blood stream. Methods for the formation of a core-shell-brush nanoparticle from an A-B-C triblock copolymer are set forth. A hydrophilic core can contain the biologic and the C Block of the copolymer. The shell can be comprised of the precipitated B Block, and the A Block can form a stabilizing brush layer. The particles can be assembled by sequential precipitations under defined mixing conditions. Presented herein are methods to tune release based on process parameters during particle assembly and triblock characteristics.

30 Claims, 6 Drawing Sheets

(56) References Cited

U.S. PATENT DOCUMENTS

| | | |
|---|---|---|
| 6,998,426 B2 | 2/2006 | L'Alloret |
| 7,052,719 B2 | 5/2006 | Bernstein |
| 7,842,308 B2 | 11/2010 | McAllister et al. |
| 7,977,024 B2 | 7/2011 | Zhou et al. |
| 8,137,699 B2 | 3/2012 | Johnson |
| 8,288,001 B1 | 10/2012 | Fan et al. |
| 8,298,581 B2 | 10/2012 | Fischer et al. |
| 8,603,514 B2 | 12/2013 | Yang |
| 8,623,329 B1 | 1/2014 | Hansen et al. |
| 8,703,196 B2 | 4/2014 | Babcock et al. |
| 9,504,658 B2 | 11/2016 | Miller et al. |
| 9,603,830 B2 | 3/2017 | Llc |
| 9,782,358 B2 | 10/2017 | Kataoka et al. |
| 10,231,937 B2 | 3/2019 | Pagels et al. |
| 11,103,461 B2 | 8/2021 | Prud'Homme et al. |
| 2004/0023393 A1 | 2/2004 | Monahan et al. |
| 2004/0052824 A1 | 3/2004 | Chacra-Vernet |
| 2004/0091546 A1 | 5/2004 | Johnson et al. |
| 2004/0236050 A1 | 11/2004 | Lundquist et al. |
| 2005/0158390 A1 | 7/2005 | Rana et al. |
| 2005/0228074 A1 | 10/2005 | Warren et al. |
| 2006/0040831 A1 | 2/2006 | Cassidy et al. |
| 2006/0057215 A1 | 3/2006 | Raiche et al. |
| 2006/0078624 A1 | 4/2006 | Zalipsky et al. |
| 2006/0159921 A1 | 7/2006 | Murthy et al. |
| 2006/0224095 A1* | 10/2006 | Claverie ............ A61K 9/1273 602/5 |
| 2006/0247383 A1 | 11/2006 | Hedrick et al. |
| 2007/0042498 A1 | 2/2007 | Ebner |
| 2007/0231355 A1 | 10/2007 | Quadir et al. |
| 2008/0145432 A1 | 6/2008 | Kakizawa et al. |
| 2008/0160305 A1 | 7/2008 | Warren et al. |
| 2008/0274194 A1 | 11/2008 | Miller et al. |
| 2009/0061009 A1 | 3/2009 | Schwarz et al. |
| 2009/0068743 A1 | 3/2009 | Turnell et al. |
| 2009/0155326 A1 | 6/2009 | Mack et al. |
| 2009/0325292 A1 | 12/2009 | Baker et al. |
| 2010/0150994 A1 | 6/2010 | Kotyla |
| 2010/0166866 A1 | 7/2010 | Fischer et al. |
| 2010/0203149 A1 | 8/2010 | Radosz et al. |
| 2010/0233251 A1 | 9/2010 | Von Andrian et al. |
| 2010/0305219 A1 | 12/2010 | Granick et al. |
| 2010/0310649 A1 | 12/2010 | Richard et al. |
| 2010/0330368 A1 | 12/2010 | Prud'homme et al. |
| 2011/0012057 A1 | 1/2011 | Lindner et al. |
| 2011/0022129 A1 | 1/2011 | Prud'homme et al. |
| 2011/0064821 A1 | 3/2011 | Catchpole et al. |
| 2011/0200828 A1 | 8/2011 | Li et al. |
| 2011/0206739 A1 | 8/2011 | Nicolosi et al. |
| 2011/0229516 A1 | 9/2011 | Ochomogo et al. |
| 2011/0236686 A1 | 9/2011 | Kitano et al. |
| 2011/0293701 A1 | 12/2011 | Bratzler et al. |
| 2012/0009267 A1 | 1/2012 | Cho et al. |
| 2012/0041150 A1 | 2/2012 | Yabu et al. |
| 2012/0121510 A1 | 5/2012 | Brem et al. |
| 2012/0171254 A1 | 7/2012 | Johnson et al. |
| 2012/0230913 A1 | 9/2012 | Johnston et al. |
| 2012/0308640 A1 | 12/2012 | Percec et al. |
| 2013/0064954 A1 | 3/2013 | Ochomogo et al. |
| 2013/0101516 A1 | 4/2013 | Zhao |
| 2013/0115272 A1 | 5/2013 | Therapeutics |
| 2013/0122058 A1 | 5/2013 | Chow et al. |
| 2013/0171208 A1 | 7/2013 | Smith et al. |
| 2013/0337078 A1 | 12/2013 | Mayer et al. |
| 2014/0037573 A1 | 2/2014 | Eliasof et al. |
| 2014/0099379 A1 | 4/2014 | Beck-Broichsitter et al. |
| 2014/0249235 A1 | 9/2014 | Brugel et al. |
| 2014/0302154 A1 | 10/2014 | Ag |
| 2014/0356443 A1 | 12/2014 | Brisander et al. |
| 2015/0086618 A1 | 3/2015 | Onyuksel et al. |
| 2015/0218198 A1 | 8/2015 | Petermann et al. |
| 2015/0283218 A1 | 10/2015 | Shea et al. |
| 2015/0290233 A1 | 10/2015 | Ltd. |
| 2015/0298084 A1 | 10/2015 | Schoeppe et al. |
| 2015/0299369 A1 | 10/2015 | Ausserre et al. |
| 2016/0235677 A1 | 8/2016 | Hoerr et al. |
| 2016/0317459 A1 | 11/2016 | Ensign et al. |
| 2016/0346266 A1 | 12/2016 | Tolleth et al. |
| 2017/0042823 A1 | 2/2017 | Prud'Homme et al. |
| 2017/0151339 A1 | 6/2017 | White et al. |
| 2017/0209386 A1 | 7/2017 | Pagels et al. |
| 2018/0009924 A1 | 1/2018 | Sadowski et al. |
| 2018/0125915 A1 | 5/2018 | Mikhail |
| 2019/0008788 A1 | 1/2019 | Prud'Homme et al. |
| 2019/0151252 A1 | 5/2019 | Pagels et al. |
| 2019/0192444 A1 | 6/2019 | Barzilay et al. |
| 2020/0023332 A1 | 1/2020 | Prud'homme et al. |
| 2020/0147032 A1 | 5/2020 | Prud'homme et al. |
| 2020/0206136 A1 | 7/2020 | Prud'homme et al. |
| 2021/0085619 A1 | 3/2021 | Baldwin et al. |
| 2021/0378980 A1 | 12/2021 | Horhota et al. |
| 2021/0379181 A1 | 12/2021 | Rauch et al. |

FOREIGN PATENT DOCUMENTS

| | | | |
|---|---|---|---|
| CN | 104042567 A | 9/2014 | |
| CN | 105213250 A | 1/2016 | |
| CN | 106750272 A | 5/2017 | |
| EP | 2962752 A1 | 1/2016 | |
| JP | 2000514791 A | 11/2000 | |
| JP | 2003513019 A | 4/2003 | |
| JP | 2008297288 A | 12/2008 | |
| JP | 2011506499 A | 3/2011 | |
| JP | 2014514275 A | 6/2014 | |
| JP | 2015129128 A | 7/2015 | |
| JP | 2015529683 A | 10/2015 | |
| JP | 2017505800 A | 2/2017 | |
| JP | 2018535228 A | 11/2018 | |
| WO | WO 1994008599 A1 | 4/1994 | |
| WO | WO 1997049387 A1 | 12/1997 | |
| WO | WO 1997049736 A2 | 12/1997 | |
| WO | WO 2001022937 A1 | 4/2001 | |
| WO | WO 2002076441 A1 | 10/2002 | |
| WO | WO 2002078674 A1 | 10/2002 | |
| WO | WO 2002092069 A1 | 11/2002 | |
| WO | WO 2009080164 A1 | 7/2009 | |
| WO | WO 2010148653 A1 | 12/2010 | |
| WO | WO 2012122544 A2 | 9/2012 | |
| WO | WO 2013023003 A1 | 2/2013 | |
| WO | WO 2013160773 A2 | 10/2013 | |
| WO | WO 2014043625 A1 | 3/2014 | |
| WO | WO 2014133172 A1 | 9/2014 | |
| WO | WO 2014165679 A1 | 10/2014 | |
| WO | WO 2015123562 A1 | 8/2015 | |
| WO | WO 2015130835 A1 | 9/2015 | |
| WO | WO-2015200054 A2 * | 12/2015 | ............ A61K 31/00 |
| WO | WO 2015200054 A9 | 12/2015 | |
| WO | WO 2016193810 A1 | 12/2016 | |
| WO | WO 2017089942 A1 | 6/2017 | |
| WO | WO 2017112828 A1 | 6/2017 | |
| WO | WO 2017/130046 A1 | 8/2017 | |
| WO | WO 2019/050969 A1 | 3/2019 | |
| WO | WO 2019055539 A1 | 3/2019 | |
| WO | WO 2019090030 A1 | 5/2019 | |
| WO | WO 2020018890 A1 | 1/2020 | |
| WO | WO 2020/227350 A1 | 11/2020 | |
| WO | WO 2020252346 A1 | 12/2020 | |
| WO | WO 2021/046078 A1 | 3/2021 | |

OTHER PUBLICATIONS

International Patent Application PCT/US2020/031579 International Search Report and Written Opinion dated Aug. 3, 2020.
International Patent Application PCT/US2020/037542 International Search Report and Written Opinion dated Sep. 11, 2020.
International Patent Application PCT/US2020/048986 International Search Report and Written Opinion dated Feb. 16, 2021.
IQQueryQuickExport search results—202004301516 (IP.com NPL search results)—downloaded Apr. 30, 2020, 4 pages.
IQQueryQuickExport search results—202004301547 (IP.com NPL search results)—downloaded Apr. 30, 2020, 2 pages.
IQQueryQuickExport search results—202004301605 (IP.com NPL search results)—downloaded Apr. 30, 2020, 5 pages.

(56) References Cited

OTHER PUBLICATIONS

IQQueryQuickExport search results—202004301643 (IP.com NPL search results)—downloaded Apr. 30, 2020, 5 pages.
IQQueryQuickExport search results—202004301659 (IP.com NPL search results)—downloaded Apr. 30, 2020, 5 pages.
IQQueryQuickExport search results—202004301700 (IP.com NPL search results)—downloaded Apr. 30, 2020, 2 pages.
Jain et al., "Peptide and Protein Delivery Using New Drug Delivery Systems", Crit. Revs. Ther. Drug Carrier Syst., vol. 30, No. 4, pp. 293-329 (2013).
Jang et al., "Bicontinuous Block Copolymer Morphologies Produced by Interfacially Active, Thermally Stable Nanoparticles", Macromols., vol. 44, pp. 9366-9373 (2011).
Jang et al., "Synthesis of thermally stable Au-core/Pt-shell nanoparticles and their segregation behavior in diblock copolymer mixtures", Soft Matter, vol. 7, pp. 6255-6263 (2011), doi: 10.1039/clsm05223c.
Jeon et al., "Cooperative Assembly of Block Copolymers with Deformable Interfaces: Toward Nanostructured Particles", Advanced Materials, vol. 20, pp. 4103-4108 (2008), doi: 10.1002/adma.200801377.
Johnson et al., "Characterization and Suitability of Therapeutic Antibody Dense Phases for Subcutaneous Delivery", Molecular Pharmaceutics, vol. 10, pp. 3582-3591 (2013).
Johnson et al., "Chemical Processing and Micromixing in Confined Impinging Jets", AIChE Journal, vol. 49, No. 9, pp. 2264-2282 (2003).
Johnson et al., "Flash NanoPrecipitation of Organic Actives and Block Copolymers using a Confined Impinging Jets Mixer," Australian Journal of Chemistry, vol. 56, No. 10, pp. 1021-1024 (2003).
Johnson et al., "Nanoprecipitation of Organic Actives Using Mixing and Block Copolymer Stabilization", Abstracts of Papers of the American Chemical Society, No. 186 (Abstract) (Sep. 2003).
Johnson et al., "Engineering the Direct Precipitation of Stabilized Organic and Block Copolymer Nonparticles as Unique Composites", Abstracts of Papers of the American Chemical Society, No. 441 (Abstract) (Sep. 2003).
Johnston et al., "Concentrated Dispersions of Equilibrium Protein Nanoclusters That Reversibly Dissociate into Active Monomers", ACS Nano, vol. 6, No. 2, pp. 1357-1369 (2012).
Kakizawa et al., "Controlled release of protein drugs from newly developed amphiphilic polymer-based microparticles composed of nanoparticles", Journal of Controlled Release, vol. 142, pp. 8-13 (2010).
Kang et al., "Pore Closing and Opening in Biodegradable Polymers and Their Effect on the Controlled Release of Proteins", Mol. Pharmaceutics, vol. 4, No. 1, pp. 104-118 (2007).
Khanvilkar et al., "Drug transfer through mucus," Advanced Drug Delivery Reviews, vol. 48, Nos. 2-3, pp. 173-193 (2001).
Kim et al., "Critical effect of freezing/freeze-drying on sustained release of FITC-dextran encapsulated within PLGA microspheres", Int'l J. Pharmaceutics, vol. 271, pp. 207-214 (2004).
Kim et al., "Multicomponent Nanoparticles via Self-Assembly with Cross-Linked Block Copolymer Surfactants", Langmuir, vol. 23, pp. 2198-2202 (2007).
Kohen, N., "Characterization of Polystyrene-block-poly(acrylic acid) Micelles In Solution and Assembled on Solid Substrates", Massachusetts Institute of Technology, Thesis, pp. 1-38 (Jun. 2005).
Kovalainen et al., "Novel Delivery Systems for Improving the Clinical Use of Peptides", Pharmacol. Rev., vol. 67, No. 3, pp. 541-561 (Jul. 2015).
Kumar et al., "Amphiphilic Janus particles at fluid interfaces", Soft Matter, vol. 9, pp. 6604-6617 (2013).
Lai et al., "Mucus-penetrating nanoparticles for drug and gene delivery to mucosal tissues," Advanced Drug Delivery Reviews, vol. 61, No. 2, pp. 158-171 (2009).
Lai et al., "Rapid transport of large polymeric nanoparticles in fresh undiluted human mucus," Proceedings National Academy of Sciences, vol. 104, No. 5, pp. 1482-1487 (Jan. 30, 2007).
Langer, R., "Drug delivery and targeting", Nature, vol. 392, No. 6679, pp. 5-10 (Apr. 30, 1998).
Lavasanifar et al., "Poly(ethylene oxide)-block-poly(L-amino acid) micelles for drug delivery", Advanced Drug Delivery Reviews, vol. 54, pp. 169-190 (2002).
Li et al., "Pharmacokinetics and Biodistribution of Nanoparticles", Molecular Pharmaceutics, vol. 5, No. 4, pp. 496-504 (2008).
Liang et al., "Preparation of nanoparticles composed of poly(gamma-glutamic acid)-poly(lactide) block copolymers and evaluation of their uptake by HepG2 cells", J. Controlled Release, vol. 105, pp. 213-225 (2005).
Liu et al., "CFD Predictions for Chemical Processing in a Confined Impinging-Jets Reactor', AlChE Journal, vol. 52, No. 2, pp. 731-744 (Feb. 2006).
Liu et al., "Janus Colloids Formed by Biphasic Grafting at a Pickering Emulsion Interface", Angew. Chem., vol. 120, pp. 4037-4039 (2008).
Liu, Y et al., "Mixing in a multi-inlet vortex mixer (MIVM) for flash nano-precipitation", Chemical Engineering Science, (2008), vol. 63, No. 11, pp. 2829-2842.
Liu et al., "Ostwald Ripening of beta-Carotene Nanoparticles", Phys. Rev. Lett., vol. 98, No. 3, p. 036102-1 - 036102-4 (2007).
Livraghi et al., "Cystic Fibrosis and Other Respiratory Diseases of Impaired Mucus Clearance", Toxicologic Pathology, vol. 35, No. 1, pp. 116-129 (2007).
Lu et al., "Hydrophobic Ion Pairing of Peptide Antibiotics for Processing into Controlled Release Nanocarrier Formulations", Molecular Pharmaceutics, vol. 15, No. 1, pp. 216-225 (2018).
Luo et al., "Synthetic DNA delivery systems," Nature Biotechnology, vol. 18, No. 1, pp. 33-37 (Jan. 2000).
Mai et al., "Controlled Incorporation of Particles into the Central Portion of Vesicle Walls", J. Am. Chem. Soc., vol. 132, p. 10078-10084 (2010).
Marcus et al., "Ion Pairing", Chemical Reviews, vol. 106, No. 11, pp. 4585-4621 (2006).
Markwalter et al., "Inverse Flash NanoPrecipitation for Biologics Encapsulation: Understanding Process Losses via an Extraction Protocol", Control of Amphiphile Self-Assembling at the Molecular Level: Supra-Molecular Assemblies with Tuned Physicochemical Properties for Delivery Applications, pp. 275-296 (Jan. 1, 2017).
Matschiner et al., "Optimization of Topical Erythromycin Formulations by Ion Pairing", Skin Pharmacology: The Official Journal of the Skin Pharmacology Society, vol. 8, No. 6, pp. 319-325 (1995).
Meyer et al., "Hydrophobic Ion Pairing: Altering the Solubility Properties of Biomolecules", Pharmaceutical Research, vol. 15, No. 2, pp. 188-193 (1998).
Mitragotri et al., "Overcoming the challenges in administering biopharmaceuticals: formulation and delivery strategies", Nat. Rev. Drug Discov., vol. 13, No. 9, pp. 655-672 (41 pages) (Sep. 2014).
Muehle et al., "Stability of Particle Aggregates in Flocculation with Polymers: Stabilitaet vonder Flockung mit Polymeren", Chemical Engineering & Processing: Process Intensification,(1991).
U.S. Appl. No. 16/253,850 U.S. Patent & Trademark Office (USPTO) Communication dated Mar. 9, 2021.
U.S. Appl. No. 16/253,850 Notice of Allowance & Notice of Allowability dated Apr. 12, 2022.
U.S. Appl. No. 16/253,850, filed Aug. 11, 2021 dated Summary of Interview of Aug. 9, 2021.
U.S. Appl. No. 16/253,850 Office Action dated Sep. 23, 2021.
U.S. Appl. No. 16/253,850 Notice of Allowance & Notice of Allowability dated Sep. 13, 2022.
U.S. Appl. No. 16/253,850 Supplemental Notice of Allowability dated Dec. 19, 2022.
U.S. Appl. No. 16/517,510 Restriction/Election Requirement dated Mar. 19, 2021.
U.S. Appl. No. 16/517,510 Office Action dated Sep. 24, 2021.
U.S. Appl. No. 16/517,510 Notice of Allowance & Notice of Allowability dated May 9, 2022.
U.S. Appl. No. 16/517,510 Notice of Allowance & Notice of Allowability dated Nov. 23, 2022.
U.S. Appl. No. 16/517,510 Notice of Allowance & Notice of Allowability dated Apr. 19, 2023.
U.S. Appl. No. 16/761,140 Office Action dated Feb. 14, 2024.
U.S. Appl. No. 16/761,140 Office Action dated Jun. 5, 2023.
U.S. Appl. No. 16/761,140 Office Action dated Feb. 8, 2022.

(56) References Cited

OTHER PUBLICATIONS

U.S. Appl. No. 16/761,140 Office Action dated Aug. 26, 2022.
U.S. Patent Application 16/761, 140 Restriction/Election Requirement dated Aug. 19, 2021.
U.S. Appl. No. 16/816,241 Office Action dated May 12, 2022.
U.S. Appl. No. 16/816,241 Restriction/Election Requirement dated Sep. 30, 2021.
U.S. Appl. No. 16/816,241 Notice of Allowance & Notice of Allowability dated Nov. 16, 2022.
U.S. Appl. No. 16/816,241 Notice of Allowance & Notice of Allowability dated Mar. 7, 2023.
U.S. Appl. No. 16/816,241 Notice of Allowance & Notice of Allowability dated Apr. 13, 2023.
U.S. Appl. No. 16/810,710 Restriction/Election Requirement dated Jan. 6, 2021.
U.S. Appl. No. 16/810,710 Office Action dated May 12, 2021.
U.S. Appl. No. 16/810,710 Office Action dated Mar. 30, 2022.
U.S. Appl. No. 17/899,157 Restriction/Election Requirement dated Oct. 30, 2023.
U.S. Appl. No. 17/899,157 Office Action dated Apr. 10, 2024.
Vyavahare et al., "Analysis of Structural Rearrangements of Poly(lactic acid) in the Presence of Water", Journal Physical Chemistry B, vol. 118, No. 15, pp. 4185-4193 (2014).
Wang et al., "Characterization of the initial burst release of a model peptide from poly(D,L-lactide-co-glycolide) microspheres", J. Controlled Release, vol. 82, pp. 289-307 (2002).
Xu et al., "Scalable method to produce biodegradable nanoparticles that rapidly penetrate human mucus", Journal of Controlled Release, vol. 170, pp. 279-286 (2013).
Yu et al., "Nanotechnology for Protein Delivery: Overview and Perspectives", J. Controlled Release, vol. 240, pp. 24-37 (32 pages) (Oct. 28, 2016).
Zandonella, "Bob Prud'homme - Flash NanoPrecipitation" http://research.princeton.edu/news/features/a/index.XML? id=6234, accessed Mar. 9, 2018, originally published Dec. 9, 2011, pp. 1-2.
Zhang et al., "Development of Nanoparticles for Antimicrobial Drug Delivery", Current Medicinal Chemistry, vol. 17, No. 5, pp. 585-594 (2010).
Zhang et al., "Amphiphilic cylindrical brushes with poly(acrylic acid) core and poly(n-butyl acrylate) shell and narrow length distribution", Polymer, vol. 44, No. 5, pp. 1449-1458 (2003).
Zhu et al., "Preparation and characterization of hCG-loaded polylactide or poly(lactide-co-glycolide) microspheres using a modified water-in-oil-in-water (w/o/w) emulsion solvent evaporation technique", J. Microencapsulation, vol. 18, No. 2, pp. 247-260 (2001).
Bilati et al., "Nanoprecipitation Versus Emulsion-based Techniques for the Encapsulation of Proteins Into Biodegradable Nanoparticles and Process-related Stability Issues", AAPS PharmSciTech, vol. 6, No. 4, Article 74, pp. E594-E604 (2005).
Hadinoto et al., "Lipid-polymer hybrid nanoparticles as a new generation therapeutic delivery platform: A review". European Journal of Pharmaceutics & Biopharmaceutics, vol. 85, No. 3, part A, pp. 427-443 (2013).
Kauffman et al., "Materials for non-viral intracellular delivery of messenger RNA therapeutics", J. Controlled Release, vol. 240, pp. 227-234 (2016).
Mueller et al., "Solid lipid nanoparticles (SLN) for controlled drug delivery—a review of the state of the art", European Journal of Pharmaceutics & Biopharmaceutics, vol. 50, No. 1, pp. 161-177 (2000).
Muheem et al., "A review on the strategies for oral delivery of proteins and peptides and their clinical perspectives", Saudi Pharmaceutical Journal, vol. 24, No. 4, pp. 413-428 (2016).
O'Reilly et al., "Cross-linked block copolymer micelles: functional nanostructures of great potential and versatility", Chemical Society Reviews, vol. 35, pp. 1068-1083 (2006).
Okuyama et al., "Preparation of functional nanostructured particles by spray drying", Advanced Powder Technol., vol. 17, No. 6, pp. 587-611 (2006).
Overbeek et al., "Phase separation in polyelectrolyte solutions. Theory of complex coacervation", Journal of Cellular Physiology, vol. 49, No. S1, pp. 7-26 (1957).
Owens et al., "Opsonization, biodistribution, and pharmacokinetics of polymeric nanoparticles", International Journal of Pharmaceutics, vol. 307, No. 1, pp. 93-102 (2006).
Pagels et al., "Inverse Flash NanoPrecipitation for Biologics Encapsulation: Nanoparticle Formation and Ionic Stabilization in Organic Solvents", ACS Publications, vol. 1271, pp. 249-274 (2017).
Pagels et al., "Polymeric nanoparticles and microparticles for the delivery of peptides, biologics, and soluble therapeutics", Journal of Controlled Release, vol. 219, pp. 519-535 & Supplemental Information (2015).
Patel et al., "A novel approach for antibody nanocarriers development through hydrophobic ion-pairing complexation", Journal of Microencapsulation, vol. 31, No. 6, pp. 542-550 (2014).
Patil et al., "Retention of trypsin activity in spermine alginate microcapsules", Journal of Microencapsulation, vol. 14, No. 4, pp. 469-474 (1997).
Pattni et al., "New Developments in Liposomal Drug Delivery", Chemical Reviews, vol. 115, No. 19, p. 10938-10966 (2015).
Peters et al., "Biotech Products in Big Pharma Clinical Pipelines Have Grown Dramatically According to the Tufts Center for the Study of Drug Development", Nov. 14, 2013, https://www.biospace.com/ ... a-clinical-pipelines-have- grown-dramatically-according-to-the-tufts-center-for-the-study-of-drug-development-/, accessed Aug. 29, 2018 (5 pages).
Pham et al., "Micellar Solutions of Associative Triblock Copolymers: Entropic Attraction and Gas-Liquid Transition", Macromolecules, vol. 32, No. 9, pp. 2996-3005 (1999).
Pinkerton et al., "Formation of Stable Nanocarriers by in Situ Ion Pairing during Block-Copolymer-Directed Rapid Precipitation", Molecular Pharmaceutics, vol. 10, No. 1, pp. 319-328 (2013).
Pitt, "The controlled parenteral delivery of polypeptides and proteins", International Journal of Pharmaceutics, vol. 59, pp. 173-196 (1990).
Pustulka et al., "Flash Nanoprecipitation: Particle Structure and Stability", Molecular Pharmaceutics, vol. 10, pp. 4367-4377 (2013).
Qi et al., "Determination of the Bioavailability of Biotin Conjugated onto Shell Cross-Linked (SCK) Nanoparticles", Journal American Chemical Society, vol. 126, pp. 6599-6607 (2004).
Reinhold et al., "Self-healing Microencapsulation of Biomacromolecules without Organic Solvents", Angew. Chem. Int. Ed. Engl., vol. 51, No. 43, pp. 10800-10803 (9 pages) (Oct. 22, 2012).
Reinhold et al., "Self-Healing Microencapsulalion of Biomacromolecules without Organic Solvents", Angewandte Chemie, vol. 124, Issue 43, p. 10958-10961 (6 pages) (Oct. 2012).
Riess et al. "Emulsifying Properties of Block Copolymers. Oil-Water Emulsions and Microemulsions", Polym. Eng. Sci., vol. 17, No. 8, pp. 634-638 (1977).
Rädler et al., "Structure of DNA-Cationic Liposome Complexes: DNA Intercalation in Multilamellar Membranes in Distinct Interhelical Packing Regimes", Science, vol. 275, No. 5301, pp. 810-814 (Feb. 7, 1997), DOI: 10.1126/ science.275.5301.810.
Saad, W.S. & Prud'homme, R.K., "Principles of nanoparticle formation by flash nanoprecipitation", Nano Today, vol. 11, No. 2, pp. 212-227 (2016).
Sahoo et al., "Characterization of Porous PLGA/PLA Microparticles as a Scaffold for Three Dimensional Growth of Breast Cancer Cells", Biomacromolecules, vol. 6, pp. 1132-1139 (2005).
Salentinig et al., "Self-Assembled Structures and pKa Value of Oleic Acid in Systems of Biological Relevance", Langmuir, vol. 26, No. 14, pp. 11670-11679 (2010). DOI: 10.1021/1a101012a.
Sato et al., "Therapeutic peptides: technological advances driving peptides into development", Current Opinion in Biotechnology, vol. 17, pp. 638-642 (2006).
Savjani, K.T. et al., "Drug Solubility: Importance and Enhancement Techniques", ISRN Pharmaceutics, vol. 2012, Article ID 195727, pp. 1-10 (2012).
Schwendeman et al., "Injectable controlled release depots for large molecules", Journal of Controlled Release, vol. 190, pp. 240-253 (37 pages) (Sep. 28, 2014).

(56) References Cited

OTHER PUBLICATIONS

Serajuddin, "Salt formation to improve drug solubility", Advanced Drug Delivery Reviews, vol. 59, No. 7, pp. 603-616 (2007).
Shah et al., Poly(glycolic acid-co-DL-lactic acid): diffusion or degradation controlled drug delivery?, Journal of Controlled Release, vol. 18, pp. 261-270 (1992).
Sheela, D.L et al., "Lauric acid induce cell death in colon cancer cells mediated by the epidermal growth factor receptor downregulation: An in silico and in vitro study", Human & Experimental Toxicology, (Epub. Apr. 3, 2019) pp. 1-9, DOI: 10.1177/0960327119839185.
Sohn et al., "Polymer prodrug approaches applied to paclitaxel", Polymer Chemistry, vol. 1, No. 6, pp. 778-792 (2010).
Solaro et al., "Targeted Delivery of Protein Drugs by Nanocarriers", Materials, vol. 3, No. 3, pp. 1928-1980 (2010).
Song et al., "A novel in situ hydrophobic ion pairing (HIP) formulation strategy for clinical product selection of a nanoparticle drug delivery system", Journal of Controlled Release, vol. 229, pp. 106-119 (2016).
Sosa et al., "Soft Multifaced and Patchy Colloids by Constrained vol. Self-Assembly", Macromolecules, vol. 49, pp. 3580-3585 (2016).
Steichen et al., "A review of current nanoparticle and targeting moieties for the delivery of cancer therapeutics", European J. Pharmaceutical Sciences, vol. 48, pp. 416-427 (2013).
Talelli et al., "Core-crosslinked polymeric micelles: Principles, preparation, biomedical applications and clinical translation", Nano Today, vol. 10, pp. 93-117 (2015).
Tang et al., "An innovative method for preparation of hydrophobic ion-pairing colistin entrapped poly(lactic acid) nanoparticles: Loading and release mechanism study", European J. Pharmaceutical Sciences, vol. 102, pp. 63-70 (2017).
Turro et al., "Spectroscopic Probe Analysis of Protein-Surfactant Interactions: The BSA/SDS System", Langmuir, vol. 11, No. 7, pp. 2525-2533 (1995).
U.S. Appl. No. 15/321,588 Notice of Allowance & Notice of Allowability dated Oct. 24, 2018.
U.S. Appl. No. 15/321,588 Office Action dated Apr. 10, 2018.
U.S. Appl. No. 15/321,588 Restriction/Election Requirement dated Dec. 1, 2017.
U.S. Appl. No. 15/321,588, filed Oct. 24, 2018 dated Summary of Examiner Interview of Oct. 9, 2018.
U.S. Appl. No. 16/064,935 Notice of Allowability dated Aug. 2, 2021.
U.S. Appl. No. 16/064,935 Notice of Allowability dated Jun. 21, 2021.
U.S. Appl. No. 16/064,935 Notice of Allowance & Notice of Allowability dated Oct. 21, 2020.
U.S. Appl. No. 16/064,935 Notice of Allowance & Notice of Allowability dated Apr. 28, 2021.
U.S. Appl. No. 16/064,935 Notice of Allowance & Notice of Allowability dated May 6, 2020.
U.S. Appl. No. 16/064,935 Restriction/Election Requirement dated Jan. 13, 2020.
U.S. Appl. No. 16/253,850 Restriction/Election Requirement dated Apr. 7, 2020.
U.S. Appl. No. 16/253,850 Office Action dated Sep. 8, 2020.
Aggarwal et al., "What's fueling the biotech engine - 2012 to 2013", Nat. Biotechnol., vol. 32, No. 1, pp. 32-39, Jan. 2014.
Ansell et al., "Modulating the Therapeutic Activity of Nanoparticle Delivered Paclitaxel by Manipulating the Hydrophobicity of Prodrug Conjugates," Journal of Medicinal Chemistry, vol. 51, No. 11, pp. 3288-3296 (2008).
Anton et al., "Aqueous-Core Lipid Nanocapsules for Encapsulating Fragile Hydrophilic and/or Lipophilic Molecules", Langmuir, vol. 25, No. 19, pp. 11413-11419 (2009).
Antonietti et al., "Polyelectrolyte-Surfactant Complexes: A New Type of Solid, Mesomorphous Material", Macromolecules, vol. 27, No. 21, pp. 6007-6011 (1994).
Antonov et al., "Entering and Exiting the Protein - Polyelectrolyte Coacervate Phase via Nonmonotonic Salt Dependence of Critical Conditions", Biomacromolecules, vol. 11, No. 1, pp. 51-59 (2010).
Arshady, "Preparation of biodegradable microspheres and microcapsules: 2. Polyactides and related polyesters", Journal of Controlled Release, vol. 17, pp. 1-22 (1991).
Babu, N.J. & Nangia, A., "Solubility Advantage of Amorphous Drugs and Pharmaceutical Cocrystals", Crystal Growth & Design, vol. 11, pp. 2662-2679 (2011).
Bailly, N. et al. "Poly(N-vinylpyrrolidone)-block-poly(vinyl acetate) as a Drug Delivery Vehicle for Hydrophobic Drugs", Biomacromolecules, vol. 13, pp. 4109-4117 (2012).
Basf, Luviscol VA Grades Technical Information, Jun. 2012, pp. 1-14.
Bilati et al., "Development of a nanoprecipitation method intended for the entrapment of hydrophilic drugs into nanoparticles", European J. Pharmaceutical Sciences, vol. 24, pp. 67-75 (2005).
Bontha et al., "Polymer micelles with cross-linked ionic cores for delivery of anticancer drugs", Journal of Controlled Release, vol. 114, pp. 163-174 (2006).
Bronich et al., "Polymer Micelle with Cross-Linked Ionic Core", J. Am. Chem Soc., vol. 127, pp. 8236-8237 (2005).
Bronich et al., "Soluble Complexes from Poly(ethylene oxide)-block-polymethacrylate Anions and N-Alkylpyridinium Cations", Macromolecules, vol. 30, pp. 3519-3525 (1997).
Bruno et al., Basics and recent advances in peptide and protein drug delivery, Therapeutic Delivery, vol. 4, No. 11, pp. 1443-1467 (45 pages) (2013).
Colombani et al., "Structure of Micelles of Poly(n-butyl acrylate)-block-poly(acrylic acid) Diblock Copolymers in Aqueous Solution," Macromolecules, vol. 40, pp. 4351-4362 (2007).
Colombani et al., "Synthesis of Poly(n-butyl acrylate)-block-poly(acrylic acid) Diblock Copolymers by ATRP and Their Micellization in Water," Macromolecules, vol. 40, pp. 4338-4350 (2007).
"The Complete Guide to Enteric Coating", https://astenzymes.com/the-complete-guide-to-enteric-coating/, pp. 1-11, accessed Aug. 11, 2020.
Crater et al., "Barrier Properties of Gastrointestinal Mucus to Nanoparticle Transport," Macromolecular Bioscience, vol. 10, No. 12, pp. 1473-1483 (2010).
Cu et al., "Drug delivery: Stealth particles give mucus the slip", Nature Materials, vol. 8, No. 1, pp. 11-13 (Jan. 2009).
D'Addio & Prud'Homme, "Controlling drug nanoparticle formation by rapid precipitation", Advanced Drug Delivery Reviews, vol. 63, No. 6, pp. 417-426 (2011).
Davies et al., "Recent advances in the management of cystic fibrosis", Archives of Disease in Childhood, vol. 99, No. 11, pp. 1033-1036 (2014).
Deng et al., "Janus Nanoparticles of Block Copolymers by Emulsion Solvent Evaporation Induced Assembly", Macromolecules, vol. 49, pp. 1362-1368 (2016).
Eghbali et al., "Rheology and Phase Behavior of Poly(n-butyl acrylate)-block-poly(acrylic acid) in Aqueous Solution", Langmuir, vol. 22, pp. 4766-4776 (2006).
Ensign et al., "Oral drug delivery with polymeric nanoparticles: The gastrointestinal mucus barriers," Advanced Drug Delivery Reviews, vol. 64, No. 6, pp. 557-570 (2012).
Erre et al., "Chromium(III) Acetate, Chromium(III) Acetate Hydroxide, or mu3-Oxo-esakis-(mu2-acetato-O,O')- triaqua-trichromium(III) Acetate?", Journal of Chemical Education, vol. 74, No. 4, pp. 432-435 (Apr. 1997).
Extended European Search Report (EESR) dated Jan. 8, 2018 in European Application No. 15811879.4.
"Enteric Coating—The Enteric Coating Process", https://www.xtend-life.com/pages/enteric-coating, pp. 1-6, accessed Aug. 12, 2020.
Etchenausia, L. et al., "RAFT/MADIX emulsion copolymerization of vinyl acetate and N-vinylcaprolactam: towards waterborne physically crosslinked thermoresponsive particles", Polymer Chemistry, Doi: 10.1039/C7PY00221A, pp. 1-28 (2017).
Foerster et al., "Amphiphilic Block Copolymers in Structure-Controlled Nanomaterial Hybrids", Advanced Materials, vol. 10, No. 3, pp. 195-217 (1998).

(56) References Cited

OTHER PUBLICATIONS

Galindo-Rodriguez et al., "Polymeric Nanoparticles for Oral Delivery of Drugs and Vaccines: A Critical Evaluation of In Vivo Studies", Critical Reviews in Therapeutic Drug Carrier Systems, vol. 22, No. 5, pp. 419-463 (2005).
Gao et al., "Core Cross-Linked Reverse Micelles from Star-Shaped Polymers", Chemistry of Materials, vol. 20, pp. 3063-3067 (2008).
Gaudana et al., "Design and evaluation of a novel nanoparticulate-based formulation encapsulating a HIP complex of lysozyme", Pharmaceutical Development & Technology, vol. 18, No. 3, pp. 752-759 (2013).
Gindy et al., "Mechanism of Macromolecular Structure Evolution in Self-Assembled Lipid Nanoparticles for siRNA Delivery", Langmuir, vol. 30, No. 16, pp. 4613-4622 (2014).
Google Scholar NPL search string - downloaded Apr. 29, 2020, 1 page.
Gregory et al., "Adsorption and flocculation by polymers and polymer mixtures", Advances in Colloid & Interface Science, vol. 169, No. 1, pp. 1-12 (2011).
Groeschel et al., "Guided hierarchical co-assembly of soft patchy nanoparticles", Nature, vol. 503, pp. 247-251 (5 p. & 11 p. Methods, Extended Data Figures 1-9, & Extended Data Table 1) (Nov. 14, 2013).
Guo, Q. et al., "Binding of dihydromyricetin and its metal ion complexes with bovine serum albumin", Biotechnology & Biotechnological Equipment, vol. 28, No. 2, pp. 333-341 (2014).
Guo, Q. et al., "Biosynthesis of gold nanoparticles using a kind of flavanol: Dihydromyricetin", Colloids & Surfaces A: Physicochem. & Engineering Aspects, vol. 441, pp. 127-132 (2014).
Guo, Q. et al., "Synthesis of dihydromyricetin-manganese (II) complex and interaction with Dna", J. Molecular Structure, vol. 1027, pp. 64-69 (2012).
Holland et al., "Polymers for Biodegradable Medical Devices, 1. The Potential of Polyesters As Controlled by Macromolecular Release Systems", Journal of Controlled Release, vol. 4, pp. 155-180 (1986).
Horigome et al., "Long-Time Relaxation of Suspensions Flocculated by Associating Polymers", Langmuir, vol. 18, No. 5, pp. 1968-1973 (2002).
HØiby, "Recent advances in the treatment of Pseudomonas aeruginosa infections in cystic fibrosis", BMC Medicine, vol. 9, No. 32, pp. 1-7 (2011).
Ilton et al., "Direct Measurement of the Critical Pore Size in a Model Membrane", Physical Review Letters, 117, Issue 25, p. 257801-1 through 257801-5 (Dec. 16, 2016).
Immordino et al., "Stealth liposomes: review of the basic science, rationale, and clinical applications, existing and potential", International Journal of Nanomedicine, vol. 1, No. 3, pp. 297-315 (2006).
International Patent Application PCT/US2015/017590 International Search Report and Written Opinion dated Jul. 16, 2015.
International Patent Application PCT/US2015/036060 International Search Report and Written Opinion dated Sep. 18, 2015.
International Patent Application PCT/US2016/068145 International Search Report and Written Opinion dated Mar. 23, 2017.
International Patent Application PCT/US2017/054779 International Search Report and Written Opinion dated Jan. 26, 2018.
International Patent Application PCT/US2018/050714 International Preliminary Report on Patentability mailed Mar. 26, 2020 (issued Mar. 17, 2020).
International Patent Application PCT/US2018/049580 International Search Report and Written Opinion dated Jan. 15, 2019.
Xu et al., "Influence of experimental parameters and the copolymer structure on the size control of nanospheres in double emulsion method", J. Polymer Research, vol. 18, pp. 131-137 (2011).
U.S. Appl. No. 18/083,458 Restriction/Election Requirement dated Aug. 1, 2024.

\* cited by examiner

TRIBLOCK COPOLYMER STABILIZERS FOR THE FORMATION OF NANOPARTICLES ENCAPSULATING SOLUBLE BIOLOGICS, THERAPEUTICS, AND IMAGING AGENTS

This application is a Section 371 U.S. National Stage of International Application No. PCT/US2019/042574, filed Jul. 19, 2019, which was published as International Publication No. WO/2020/018890 on Jan. 23, 2020, which claims the benefit of U.S. Provisional Application No. 62/700,854, filed Jul. 19, 2018, the specification of which is hereby incorporated by reference in its entirety.

This invention was made with government support under Grant No. DGE-1148900 awarded by the National Science Foundation. The government has certain rights in the invention.

FIELD OF THE INVENTION

The present invention relates to a process of making nanoparticles having a hydrophilic core and methods to modify release of an encapsulated hydrophilic compound.

BACKGROUND OF THE INVENTION

Biologics have enabled more targeted intervention in disease progression when compared to traditional small molecule drugs. The success of this new field of therapeutics is reflected in its growing importance in the pharmaceutical market. In 2012, the yearly growth rate in US sales for biologics was seven times higher than for total pharmaceutical sales, and by 2019 the market is predicted to surpass $200 billion (Aggarwal S. What's fueling the biotech engine—2012 to 2013. Nat Biotechnol. 2014; 32(1):32-39. Yu M, Wu J, Shi J, Farokhzad O C. Nanotechnology for protein delivery: Overview and perspectives. J Control Release. 2015; 240:24-37.) The success of these therapeutics is undermined by delivery challenges. Biologics are often rapidly cleared from the blood, limiting the window when drug concentrations are therapeutically effective. Consequently, frequent injections are often necessary. (Kovalainen M, et al. Novel Delivery Systems for Improving the Clinical Use of Peptides. Pharmacol Rev. 2015; 67(3):541-561.) There are nearly 12 billion injections administered globally per year, each of which carries the risk of an adverse event, including infection.

The term "biologic" can encompass a range of therapeutics including peptides, oligonucleotides, polypeptides, polypeptide antibiotics, proteins, and antibodies. For example, a peptide may include a sequence of 1 to 40 amino acids. In an expanded use within this document, the term "biologic" is also used to refer to any water soluble molecules including dyes and small molecule saccharides which may also be used in this invention.

While humanized antibodies may be long circulating, proteins and peptides can be cleared from the bloodstream in a matter of minutes either due to renal clearance or enzymatic degradation (A. K. Sato, M. Viswanathan, R. B. Kent, C. R. Wood, Therapeutic peptides: technological advances driving peptides into development, Curr. Opin. Biotechnol. 17 (2006) 638-642). Therefore, delivery and extended release can require encapsulation of the biologic into nanoparticles (NPs) to provide additional protection. NPs can be defined as having sizes below 400 nm, making them prospects for injectable formulations. Requirements of NPs are high loading, high encapsulation efficiency, and an appropriate release profile of the encapsulated biologic therapeutic. These particles are commonly delivered parenterally. Examples of carriers include hydrogel carriers composed of water soluble polymers and non-swellable carriers composed of hydrophobic or solid matrices.

SUMMARY OF THE INVENTION

A method of the invention for encapsulating water soluble molecules using rapid, controlled precipitation is presented. Water soluble molecules—including peptides, proteins, DNA, RNA, non-biologic therapeutics, polysaccharide-based therapeutics (e.g., tobramycin) and imaging agents—precipitate into nanoparticles that are protected by a triblock copolymer stabilizing agent. These particles may be covalently or non-covalently stabilized. The particles thus made are colloidally stable in a first non-polar nonprocess solvent phase. The particles are further processed in a polar reforming solvent. The nanoparticles thus produced release the encapsulated biologic in aqueous buffer with tunable profiles that depend upon processing conditions, crosslinking agents used to stabilize the nanoparticle and the chemistry of the triblock copolymer used for stabilization.

The copolymer may be a triblock copolymer comprising Blocks A, B, and C. For example, the copolymer can have the form A-B-C, and each of Blocks A, B, and C is chemically distinct from the other blocks or distinct on the basis of solubility. One block type—for example Block C—can be grafted onto Block B. The block copolymer has amphiphilic character. Block A is soluble in the polar reforming solvent and in the nonprocess solvent. Block B precipitates in the reforming solvent and is soluble in the nonprocess solvent. Block C is insoluble in the nonprocess solvent so that it precipitates upon mixing of the water soluble agent solution, copolymer solution, and nonprocess solvent.

The nanoparticles are composed of a hydrophilic core containing the biologic and Block C of the stabilizing polymer, and a hydrophobic shell composed of Blocks A and B of the stabilizing polymer. Because these nanoparticles have a hydrophilic core and a hydrophobic shell, they may be termed "inverse nanoparticles" (however, at times, these nanoparticles may be simply referred to as "nanoparticles").

The A-B-C triblock copolymer can be synthesized through a number of routes. One method is through the sequential polymerization of the blocks. For example, Block A could be used as the macroinitiator for Block B. In turn, the A-B diblock copolymer could be used as the macroinitiator for Block C. The polymer synthesis method may not matter provided that the final polymer is composed of three regions (A, B, and C) distinguished by their differential solubilities.

A method of the invention for encapsulating a water soluble agent, also termed a water soluble active, includes dissolving the water soluble agent and a copolymer in a polar process solvent or mixture of polar process solvents to form a first process solution. The water soluble active can have a solubility in water of greater than 1 mg/mL and/or a log P value of less than 2. Examples of water soluble actives includes proteins (e.g., lysozyme and ovalbumin), polypeptides, linear polypeptides (e.g., proteins), cyclic polypeptides (e.g., vancomycin), branched polypeptides, glycosylated peptides (e.g., vancomycine), and other biologics and nonbiologic molecules. For example, the water soluble active can have a molecular weight of from about 100 Da, 200 Da, 500 Da, 1000 Da, 2000 Da, 5000 Da, 10000 Da, 20000 Da, and 40000 Da to about 1000 Da, 2000 Da, 5000

Da, 10000 Da, 20000 Da, 40000 Da, 100 kDa, 200 kDa, 500 kDa, and 1000 kDa. Alternatively, the water soluble agent may be dissolved in a first polar process solvent to form a water soluble agent solution, and the copolymer may be dissolved in a second polar process solvent to form a copolymer solution. That is, a method of the invention includes dissolving the water soluble agent in a polar process solvent stream and the copolymer in a separate polar solvent stream. The first polar process solvent and the second polar process solvent may be the same or different. The first process solution (or the water soluble agent solution and the copolymer solution) can be continuously mixed with a nonprocess solvent to form a mixed solution from which a nanoparticle ("inverse nanoparticle") assembles and precipitates. The multiple polar process solutions can be continuously mixed with a nonprocess solvent as described above. The nonprocess solvent is or can be less polar than the polar process solvent or solvents. The process solution is or can be more polar than the nonprocess solvent.

In an embodiment according to the invention, if the polar process solvent or solvents are mixed with the nonprocess solvent at the ratios appropriate for nanoparticle formation, the polar process solvents will either be completely miscible in the nonprocess solvent, or if the solutions are not completely miscible the ratio of the final polar phase to nonprocess solvent phase after mixing will be less than 20%. This test of solvent quality is conducted in the absence of the biologic or stabilizing block copolymer. That is, the amount of a polar first process solvent, the amount of a second polar process solvent, and the amount of a nonprocess solvent, when mixed in the absence of the water soluble active or the triblock copolymer, yields a mixture of a single phase or a mixture of which a polar phase is less than 20% of a second phase that is less polar than the polar phase.

In a method of the invention, the water soluble agent can be a biologic material, an amino acid, a peptide, a protein, DNA, RNA, a saccharide, a polysaccharide, glutathione, tryptophan, a lysozyme, glucagon-like peptide-1 (GLP-1), a small molecule therapeutic, tobramycin, vancomycin, an imaging agent, eosin Y, tartrazine, a metal chelate, a gadolinium chelate, gadolinium diethylene triamine pentaacetic acid (GD-DTPA), ovalbumin, or combinations.

The triblock copolymer can consist of a Block C that is a more polar polymer region soluble in the polar process solvent. For example, this Block C more polar region can include anionic residues (units or monomers), poly(acrylic acid) (PAA), hyaluronic acid, poly(glutamic acid), poly(aspartic acid), or combinations. In an embodiment Block C contains anionic groups which enable crosslinking, e.g., crosslinking by metal ions, ionic crosslinking, or crosslinking with an organic compound, such as tetraethylene pentamine (TEPA), of the interior Block C of the final nanoparticles. In an embodiment the anionic groups are carboxylic acids from glutamic acid or aspartic acid residues.

In an embodiment, the Block C more polar region of the copolymer includes at least one cationic more polar region. For example, this cationic more polar region may include cationic residues, such as chitosan polymer domains, histadine lipids, histamines, spermadines, polyethylene-imines, or combinations.

For example, the at least one more polar region of the polymer, Block C, can include polysaccharides or polypeptides such polyserine, polythreonine, polyglutamine and others, or combinations. Block C can consist of combinations of these different molar polar residue classes such that the residues are spatially distinct and not soluble in the nonprocess solvent.

In some embodiments, the copolymer can include a Block B consisting of at least one less polar region (region that is less polar) that includes poly(n-butyl acrylate) (PBA), poly (lactic acid) (PLA), poly(caprolactone) (PCL), poly(lactic-co-glycolic acid) (PLGA), poly(propylene sulfide), polyanhydrides, polypeptides, lipid or phospholipid grafted units, or cholesterol grafted units, or combinations.

In some embodiments, the copolymer can include a Block A consisting of at least one more polar region that is soluble in the nonprocess solvent and the reforming solvent. For example, poly(ethylene glycol) (PEG), poly(propylene oxide (PPO), poly(vinyl pyrrolidone), poly(N-(2-hydroxypropyl) methacrylamide), dextrans, starches, polysaccharides, polypeptides, or combinations thereof.

In an embodiment, the copolymer is poly(ethylene glycol)-b-poly(lactic acid)-b-poly(aspartic acid) (PEG-PLA-PAspA). In another embodiment, the copolymer is poly (ethylene glycol)-b-poly(lactic acid)-b-poly(glutamic acid) (PEG-PLA-PGlu). In another embodiment, the copolymer is poly(propylene oxide)-b-poly(lactic acid)-b-poly(aspartic acid) (PPO-PLA-PAspA). In another embodiment, the copolymer is poly(propylene oxide)-b-poly(lactic acid)-b-poly (glutamic acid) (PPO-PLA-PGlu).

In a method of the invention, the polar process solvent can be water, an alcohol, methanol, ethanol, acetone, acetonitrile, glycol ethers, dimethyl sulfoxide (DMSO), dimethylformamide (DMF), N-methyl pyrrolidone (NMP), or combinations. Glycol ethers include: ethylene glycol monomethyl ether (2-methoxyethanol, $CH_3OCH_2CH_2OH$), ethylene glycol monoethyl ether (2-ethoxyethanol, $CH_3CH_2OCH_2CH_2OH$), ethylene glycol monopropyl ether (2-propoxyethanol, $CH_3CH_2CH_2OCH_2CH_2OH$), ethylene glycol monoisopropyl ether (2-isopropoxyethanol, $(CH_3)_2CHOCH_2CH_2OH$), ethylene glycol monobutyl ether (2-butoxyethanol, $CH_3CH_2CH_2CH_2OCH_2CH_2OH$), ethylene glycol monophenyl ether (2-phenoxyethanol, $C_6H_5OCH_2CH_2OH$), ethylene glycol monobenzyl ether (2-benzyloxyethanol, $C_6H_5CH_2OCH_2CH_2OH$), diethylene glycol monomethyl ether (2-(2-methoxyethoxy)ethanol, methyl carbitol, $CH_3OCH_2CH_2OCH_2CH_2OH$), DEG monobutyl ether (2-(2-ethoxyethoxy)ethanol, butyl carbitol, $CH_3CH_2OCH_2CH_2OCH_2CH_2OH$), diethylene glycol monoethyl ether (2-(2-ethoxyethoxy)ethanol, carbitol cellosolve, $CH_3CH_2OCH_2CH_2OCH_2CH_2OH$, diethylene glycol mono-n-butyl ether (2-(2-butoxyethoxy)ethanol, and $CH_3CH_2CH_2CH_2OCH_2CH_2OCH_2CH_2OH$.

In a method of the invention there can be more than one polar process solvent used.

In a method of the invention, the nonprocess solvent can be chloroform, dichloromethane, an alkane, hexane, an ether, diethyl ether, tetrahydrofuran (THF), toluene, acetone, or combinations. For example, the nonprocess solvent can be chloroform, dichloromethane, acetone, or combinations. For example, the polar process solvent and the nonprocess solvent can be miscible. In an embodiment, the process and nonprocess solvents are completely miscible at the volume ratios used in the nanoparticle formation process. Alternatively, in another embodiment, the process solvent is substantially soluble in the nonprocess solvent, where substantially soluble is defined as having 80% by volume of the process solvent miscible in the nonprocess solvent under volume ratios used in the nanoparticle formation process.

In a method of the invention, a time of mixing of the process solution with the nonprocess solvent is less than an assembly time of the nanoparticle. For example, the water soluble agent and the copolymer can have a supersaturation level in the solution ranging from 10 to 10,000. For example, the nanoparticle can have a size ranging from about 40 nm to about 400 nm. For example, the nanoparticle can have a size ranging from about 40 nm to about 900 nm.

A method of the invention includes stabilizing the nanoparticle core through crosslinking of the copolymer. For example, the nanoparticle can be crosslinked during assembly of the nanoparticle. For example, the nanoparticle can be crosslinked after assembly of the nanoparticle. The crosslinking can be covalent crosslinking. For example, the crosslinking can be disulfide crosslinking. The crosslinking can involve as cleavable ester linkage of the types described in U.S. patent application Ser. No. 13/969,449, Particulate Constructs for Release of Active Agents, Lawrence Mayer, et al. The crosslinking can be non-covalent. For example the crosslinking can be ionic, chelation, acid-base, or hydrogen bonding crosslinking.

A crosslinking agent can be added to crosslink the copolymer. For example, the crosslinking agent can be added to crosslink a portion of the copolymer of anionic functionality. For example, the crosslinking agent can be an alkaline earth halide, a magnesium halide, magnesium chloride, a calcium halide, calcium chloride, a transition metal halide, an iron halide, iron(III) chloride, spermine, or combinations. For example, the crosslinking agent can be a metal acetate, an alkaline earth acetate, a transition metal acetate, calcium acetate, or combinations. For example, the crosslinking agent can be chromium(III) acetate, or another chromium (III) salt. For example, the water soluble agent can include tobramycin and the tobramycin can crosslink the copolymer. Other bio-compatible multi-cationic water soluble agents may be used as crosslinking agents, for example, to crosslink anionic sections of the copolymer. One example is tetraethylene pentamine.

If Block C includes cationic functional groups, then crosslinking may be achieved by the addition of polyanionic components. Examples of these are poly(acrylic acid) (PAA), hyaluronic acid, poly(glutamic acid), poly (aspartic acid), citric acid, polycitric acid, anionic oligonucleotides, and multi-valent anions.

A pH modifying agent may be added during the assembly process or after the assembly process to modify crosslinking. For a polyanionic Block C, the agent may be ammonia, an organic amine, triethylamine, sodium hydroxide or inorganic bases or organic bases. For a polycationic Block C, agents may be acetic acid, trifluoroacetic acid, hydrochloric acids, organic acids, or inorganic acids.

A method of the invention includes combining the inverse nanoparticle dispersion with a reforming solvent. Block A is soluble in the reforming solvent, and Block B is insoluble in the reforming solvent. After the combination with the reforming solvent, the core of the inverse nanoparticle is comprised of Block B and Block C, and the stabilizing polymer brush of the nanoparticle is Block A. Methods known to the field, such as distillation, can be used to remove residual nonprocess solvent after reforming.

In a method of the invention, the reforming solvent can be a more polar solvent, water, alcohols, methanol, ethanol, glycol ethers, or combinations. Water can contain salts such as sodium chloride, or buffer components such as a phosphate or tris, or cryoprotectants or osmolytes such as sucrose, trehalose, or cyclodextrin.

In an embodiment, Block A can be poly(ethylene glycol) PEG, Block B can be poly(lactic acid) (PLA), and the reforming solvent can be water.

In a method of the invention, the nonprocess solution that is largely immiscible with water can first be treated with a biphasic water extraction. This unit operation removes residual polar process solution. The water can contain a species to modify the osmotic pressure. The osmolyte can be a salt, sodium chloride, potassium chloride, or other inorganic or organic salts. The osmolyte can be a saccharide, sucrose, trehalose, glucose, or other organic compound. The water can contain a buffer to modify solution pH.

In a method of the invention, the nonprocess solution can be exchanged to a second nonprocess solvent before exposure to the reforming solvent. The second nonprocess solvent can be acetone, tetrahydrofuran, alcohols, methanol, ethanol, glycofurol, glycol ethers, or combinations. The second nonprocess solvent can be a good solvent for Block B and Block A and be miscible with the reforming solvent. It must be a nonsolvent for the encapsulated compound. If Block C is crosslinked, the second nonprocess solvent can be a good solvent for Block C. The second nonprocess solvent can be a nonsolvent for Block C. For example, acetone can be a second nonprocess solvent when Block C is poly(aspartic acid) and Block B is poly(lactic acid).

This solvent exchange can be completed by any suitable process known in the art. For example, this exchange can be a solvent swap by distillation. In some embodiments, this exchange is by put-and-take vacuum distillation. The particle solution in the second nonprocess solvent can be mixed with the reforming solvent in a rapid mixing step. In one embodiment, the second nonprocess solvent is acetone and the reforming solvent is water. In one embodiment, the second nonprocess solvent is THF and the reforming solvent is water.

In a method of the invention, the first nonprocess solution can be directly mixed with a reforming solvent without performing an extraction. The mixing can be rapid or the mixing can be uncontrolled. In some embodiments, the residual nonprocess solvent can be removed. In a method of the invention, the nonprocess solvent can be removed by evaporation.

The methods of this invention enable the formation of nanoparticles stabilized by a triblock copolymer with unexpected release profiles. The use of a triblock copolymer imparts different release kinetics than a formulation with identical composition but formed from two separate diblock copolymers using methods described in International Patent Application Publication WO/2015/200054. International Patent Application Publication WO 2017/112828 A1 does not anticipate that temperature would have a significant impact on release. That discovery, and how it can be used to design release is presented in the present patent. It was found that the temperature of reforming and residual solvent removal was important for controlling release. One knowledgeable in the art might expect that lower temperature would impart improved encapsulation efficiency and lowered shell mobility during processing. However, it was found that process temperature below the $T_g$ of the hydrophobic block in the process conditions results in very rapid release upon heating to the release temperature of 37° C. Examples provided herein are intended to illustrate these findings but should not be construed as limiting the application of the invention to these conditions alone.

In a method of the invention, hydrophobic compounds can be incorporated into the nanoparticles using the first nonprocess solvent to drive precipitation. Hydrophobic compounds can be incorporated into the nanoparticles using the reforming solvent to drive precipitation of the compound. The association of the hydrophobic compound with the nanoparticle can be achieved in an analogous fashion to U.S. Pat. No. 8,137,699 B2. For example, the hydrophobic compound can be a lipid, or alpha-tocopherol, or rapamycin, or a long-chain alcohol, or a fatty acid, or a lipopolysaccharide, poly(lactic acid), poly(lactic-co-glycol acid), or any compound that is nearly insoluble in water or prefers to self-assemble in water. Without being limited by theory, the hydrophobic compound is incorporated with a layer containing Block B.

For example, the hydrophobic compound can be a phosphatidylcholine and can be encapsulated by using acetone as a first nonprocess solvent.

As a second example, the hydrophobic compound can be a phosphatidylcholine that is incorporated by dissolving it with the nanoparticles in the first nonprocess solvent, such as chloroform. The solution can then be solvent exchanged to acetone or THF and then rapidly mixed with a reforming solvent such as water. A mixer is used such that the mixing time is faster than the assembly time of the components. Any mixer known in the art, such as a confined impinging jets mixer or a multi-inlet vortex mixer can be used.

A reformed polymer inverse nanoparticle that encapsulates a water soluble active is produced through a method of the invention including dissolving the water soluble active in an amount of a first process solvent to form a first process solution and dissolving a triblock copolymer in an amount of a second process solvent to form a second process solution, continuously mixing the first process solution and the second process solution with an amount of a nonprocess solvent to form a first nanoparticle solution comprising a polymer inverse nanoparticle having a core and a shell and a first nanoparticle solvent, using the first nanoparticle solution as an intermediate solution, adding a second nonprocess solvent to the first nanoparticle solution to form the intermediate solution, or exchanging the first nanoparticle solvent with the second nonprocess solvent to form the intermediate solution, and continuously mixing the intermediate solution with a reforming solvent to form a reformed nanoparticle solution comprising the reformed polymer inverse nanoparticle having a core and a shell.

The triblock copolymer can be a linear [Block A]-[Block B]-[Block C] copolymer.

Block A can be selected from the group consisting of poly(ethylene glycol) and poly(propylene oxide); Block B can be hydrophobic and can be selected from the group consisting of poly(lactic acid), poly(L-lactide), poly(D-lactide), poly(D,L-lactide), poly(glycolic acid), poly(lactic-co-glycolic acid), poly(caprolactone), poly(hydroxyalkanoate), poly(3-hydroxybutyrate), and poly(3-hydroxybutyrate-co-3-hydroxyvalerate); and Block C can be hydrophilic and can be selected from the group consisting of poly(aspartic acid) and poly(glutamic acid). Block A can be soluble in the polar process solvent, first process solvent, or second process solvent, can be soluble in the nonprocess solvent, and can be soluble in the reforming solvent. Block B can be soluble in the nonprocess solvent and can be insoluble in the reforming solvent. Block C can be soluble in the first process solvent, can be soluble in the second process solvent, and can be insoluble in the nonprocess solvent. The water soluble active and Block C can be in the core of the polymer inverse nanoparticle and can be in the core of the reformed polymer inverse nanoparticle.

The first process solution can be more polar than the nonprocess solvent. The second process solution can be more polar than the nonprocess solvent. The reforming solvent can be more polar than the intermediate solution. The amount of the first process solvent, the amount of the second process solvent, and the amount of the nonprocess solvent, when mixed in the absence of the water soluble active or the triblock copolymer, can yield a mixture of a single phase or a mixture of which a polar phase is less than 20% of a second phase that is less polar than the polar phase.

The polymer inverse nanoparticle Block B and Block A can extend away from the core into the first nanoparticle solvent and for the reformed polymer inverse nanoparticle Block B can be collapsed onto the surface of the core and Block A can extend away from the core into the reforming solvent.

In an method according to the invention, continuously mixing the intermediate solution with the reforming solvent does not induce precipitation of the reformed polymer inverse nanoparticle and the diameter of the reformed polymer inverse nanoparticle is no less than 50% of the diameter of the polymer inverse nanoparticle and is no more than 50% greater than the diameter of the polymer inverse nanoparticle.

Block A can have a molecular weight in the range of from 0.2 kDa to 100 kDa, from 0.5 kDa to 50 kDa, from 1 kDa to 20 kDa, from 2 kDa to 10 kDa, or of about 5 kDa. Block B can have a molecular weight in the range of from 0.5 kDa to 400 kDa, 1 kDa to 200 kDa, from 2 kDa to 100 kDa, from 5 kDa to 40 kDa, from 10 kDa to 20 kDa, of about 10 kDa, or of about 20 kDa. Block C can have a molecular weight in the range of from 0.2 kDa to 100 kDa, from 0.5 kDa to 50 kDa, from 1 kDa to 20 kDa, from 2 kDa to 10 kDa, or of about 5 kDa.

Block A can be poly(ethylene glycol).

Block B can be poly(lactic acid), poly(lactic-co-glycolic acid), or poly(caprolactone). Block C can be poly(aspartic acid) or poly(glutamic acid).

Block A can have a molecular weight in the range of from 1 kDa to 10 kDa, from 2 kDa to 8 kDa, or of about 5 kDa. Block B can have a molecular weight in the range of from 2 kDa to 100 kDa, 5 kDa to 50 kDa, from 10 kDa to 20 kDa, of about 10 kDa, or of about 20 kDa. Block C can have a molecular weight in the range of from 1 kDa to 10 kDa, from 2 kDa to 8 kDa, or of about 5 kDa.

Block A can be poly(ethylene glycol) (PEG); Block B can be poly(lactic acid) (PLA); and Block C can be poly(aspartic acid) (PAsp).

Block A can have a molecular weight in the range of from 1 kDa to 10 kDa, from 2 kDa to 8 kDa, or of about 5 kDa. Block B can have a molecular weight in the range of from 2 kDa to 100 kDa, 5 kDa to 50 kDa, from 10 kDa to 20 kDa, of about 10 kDa, or of about 20 kDa. Block C can have a molecular weight in the range of from 1 kDa to 10 kDa, from 2 kDa to 8 kDa, or of about 5 kDa.

The polymer inverse nanoparticle can have the core including the water soluble active and block C and can have the shell including block A and block B. The reformed polymer inverse nanoparticle can have the core including the water soluble active, block B, and block C and can have the shell including block A.

A lipid can be dissolved in the first process solution or the second process solution.

The first process solvent and the second process solvent can be the same solvent and together can be a single process solvent, The water soluble active and the triblock copolymer can be dissolved in the single process solvent to form a single process solution.

The single process solution can represent (for example, can be) the first process solution and the second process solution.

The single process solution can be continuously mixed with the amount of the nonprocess solvent to form the first nanoparticle solution including a polymer inverse nanoparticle having a core and a shell and a first nanoparticle solvent.

A second nonprocess solvent can be added to the first nanoparticle solution to form the intermediate solution. The second nonprocess solvent can be the same solvent as the single process solvent.

The first nanoparticle solvent can be exchanged with the second nonprocess solvent to form the intermediate solution. The first nanoparticle solvent can be not miscible with the reforming solvent.

The first process solvent can be dimethylsulfoxide (DMSO), propanol, ethanol, methanol, water, or a combination. The second process solvent can be dimethylsulfoxide (DMSO), propanol, ethanol, methanol, water, or a combination. The nonprocess solvent can be dichloromethane, chloroform, acetone, tetrahydrofuran (THF), or a combination. The second nonprocess solvent can be dichloromethane, chloroform, acetone, tetrahydrofuran (THF), or a combination. The reforming solvent can be water, methanol, ethanol, propanol, or a combination.

The water soluble active can be a linear polypeptide or a cyclic polypeptide.

The first process solvent can be completely miscible with the nonprocess solvent. The second process solvent can be completely miscible with the nonprocess solvent.

The continuous mixing can be through a flash nanoprecipitation process.

The method of the invention can further include crosslinking block C.

The method of the invention can further include ionically crosslinking block C with an organic compound.

The method of the invention can further include removing the nonprocess solvent from the reformed nanoparticle solution.

The method of the invention can further include identifying the desired rate of release of the water soluble active from the reformed polymer inverse nanoparticle and continuously mixing the intermediate solution with the reforming solvent at a temperature in the range of from 1° C. to 10° C., in the range of from 4° C. to 8° C., or at about 5° C. to achieve a fast rate of release, or continuously mixing the intermediate solution with the reforming solvent at a temperature in the range of from 15° C. to 35° C., in the range of from 17° C. to 30° C., in the range of from 20° C. to 25° C., or at about 20° C. to achieve a slow rate of release.

The triblock copolymer can be poly(ethylene glycol)-poly(lactic acid)-poly(aspartic acid); the water soluble active can be a polypeptide; the single process solvent can be DMSO or a solution of DMSO and water; and the nonprocess solvent can be dichloromethane or chloroform.

Following formation of the first nanoparticle solution, the poly(aspartic acid) block can be crosslinked through addition of tetraethylene pentaamine, and the first nanoparticle solvent can be exchanged with a second nonprocess solvent to form the intermediate solution. The second nonprocess solvent can be acetone. The reforming solvent can be water. The reforming solvent can be methanol.

The triblock copolymer can be poly(ethylene glycol)-poly(lactic acid)-poly(aspartic acid); the water soluble active can be a polypeptide; the single process solvent can include DMSO or a solution of DMSO and water; and the nonprocess solvent can be acetone. Following formation of the first nanoparticle solution, the poly(aspartic acid) block can be crosslinked through addition of tetraethylene pentaamine, and the second nonprocess solvent can be added to the first nanoparticle solution. The second nonprocess solvent can be acetone. The reforming solvent can be water.

A lipid can be dissolved into the single process solution. The single process solvent can include DMSO, ethanol, and water.

The triblock copolymer can be poly(ethylene glycol)-poly(lactic acid)-poly(aspartic acid); the water soluble active can be a polypeptide; the first process solvent can be a solution of DMSO and water; the second process solvent can be DMSO; and the nonprocess solvent can be a solution of tetrahydrofuran (THF) and chloroform. Following formation of the first nanoparticle solution, the poly(aspartic acid) block can be crosslinked, and the first nanoparticle solvent can be exchanged with a second nonprocess solvent to form the intermediate solution. The second nonprocess solvent can be acetone. The reforming solvent can be water.

A poly(ethylene glycol)-poly(lactic acid)-poly(aspartic acid) block copolymer (PEG-PLA-PAsp) is synthesized with a method according to the invention including providing methoxy-poly(ethylene glycol)-hydroxyl (mPEG-OH), growing the PLA block from the hydroxyl end of the mPEG-OH through ring opening polymerization to form mPEG-PLA-OH, converting the mPEG-PLA-OH to form mPEG-PLA-NH$_2$, reacting the mPEG-PLA-NH$_2$ with β-Benzyl L-aspartic acid N-carboxyanhydride (Benzyl-Asp-NCA) to form mPEG-PLA-PAsp(Benzyl) (with benzyl-protected PAsp acid groups), and removing the benzyl protecting groups to form mPEG-PLA-PAsp, The mPEG-PLA-OH can be formed by adding lactide monomer and a catalyst (for example, 4-(dimethylamino)pyridine (DMAP)) to fully dried mPEG-OH in chloroform as the solvent, purifying and recovering the mPEG-PLA-OH through precipitations in ice-cold methanol and isopropanol, and optionally drying the mPEG-PLA-OH.

The mPEG-PLA-NH$_2$ can be formed by conjugating the acid group of Boc-protected glycine (Boc-Gly) to the hydroxyl end of the mPEG-PLA-OH to form mPEG-PLA-Gly-Boc by using N-(3-dimethylaminopropyl)-N'-ethylcarbodiimide hydrochloride with DMAP as a catalyst in dry chloroform, purifying and recovering the mPEG-PLA-Gly-Boc by precipitations in ice-cold isopropyl alcohol, removing the Boc group with trifluoroacetic acid in dry dichloromethane (DCM), recovering the mPEG-PLA-NH2 by precipitations in cold diethyl ether, and optionally desalting to convert the polymer end amine to the free-base form.

The benzyl protecting groups can be removed by adding concentrated HBr in acetic acid to the mPEG-PLA-PAsp (Benzyl) in chloroform to form mPEG-PLA-PAsp. The mPEG-PLA-PAsp can be purified and recovered through precipitation in ice-cold diethyl ether.

DETAILED DESCRIPTION

Figure 1:
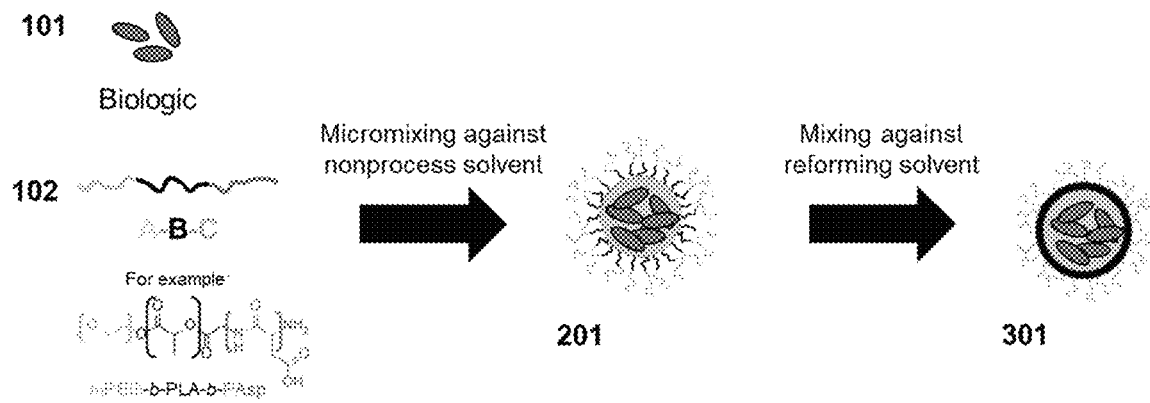
FIG. 1 illustrates process steps schematically. An encapsulated biologic 101 and a triblock copolymer 102 are rapidly mixed with a nonsolvent to produce inverse nanoparticle 201. Additional processing into a reforming results in precipitation of Block B to form the final nanoparticle 301.
Figure 2:
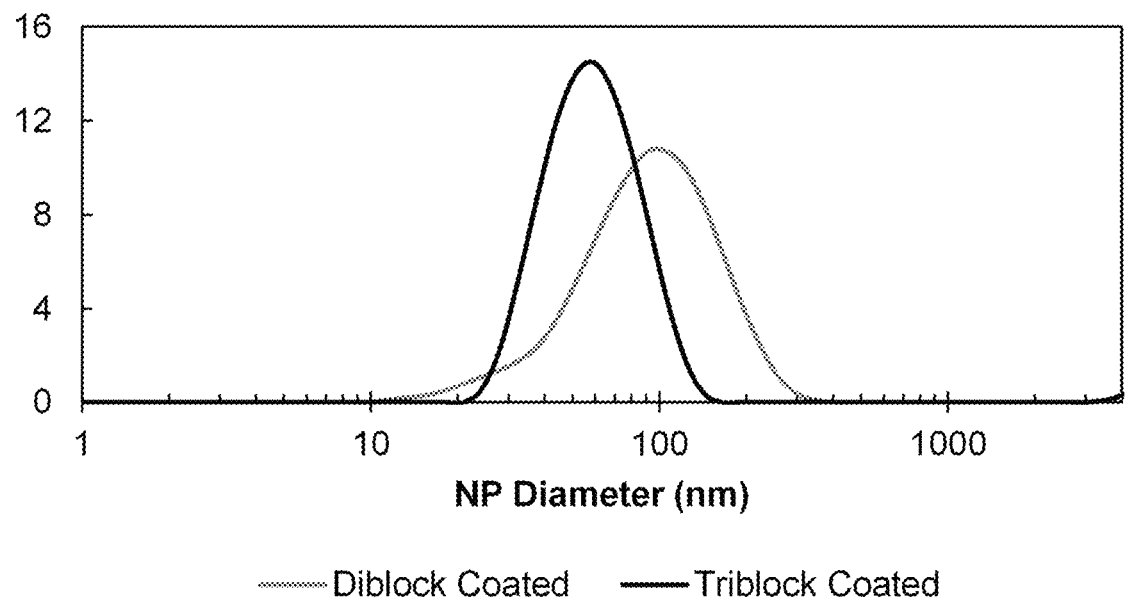
FIG. 2 depicts the dynamic light scattering (DLS) size distributions for similar formulations made according to Example 1. The encapsulated material was vancomycin. A smaller empty nanoparticle population is visible for the diblock coated particles, where a simple diblock copolymer was used to form the inverse nanoparticles prior to addition of a PLA-PEG diblock in a coating step. A portion of this polymer does not assemble to coat the inverse nanoparticle but is lost to empty nanoparticles.

Embodiments of the invention are discussed in detail below. In describing embodiments, specific terminology is employed for the sake of clarity. However, the invention is not intended to be limited to the specific terminology so selected. A person skilled in the relevant art will recognize that other equivalent parts can be employed and other methods developed without parting from the spirit and scope of the invention. All references cited herein are incorporated by reference as if each had been individually incorporated.

In this specification, the terms "nanoparticles" (NPs), "particles", and "nanocarriers" are used interchangeably, unless a distinction is indicated by the context. Particles according to the invention that have hydrophilic or more polar cores are at times referred to as "inverse particles", to contrast them with particles that have hydrophobic or less polar cores. However, for the sake of brevity, when the context indicates that particles having hydrophilic or more polar cores according to the invention are being discussed, these may be simply referred to as "particles" or "nanoparticles".

Nanoparticles are particles with hydrodynamic mass average diameters as determined by dynamic light scattering to be between 10 nm and 800 nm, for example, between 10 nm and 800 nm.

All solvents are miscible to some degree in each other. Miscible solvents are used in the initial nanoparticle precipitation process. "Miscible" solvents as referred to herein are those that when mixed at the ratios used in the nanoparticle formation process or the microparticle process would produce solutions that have no more than 20% of the volume of the minor phase (e.g., a polar process solvent) not dissolved in the majority phase. Completely miscible solvents as referred to herein are those that when mixed at the ratios used in the nanoparticle formation process or the microparticle process would produce solutions with no phase separation. "Immiscible" solvents as referred to herein are those that when mixed at the volume ratios used in the process produce less than 20% reduction in the volume of the minor phase due to solubilization into the majority phase.

International Patent Application Publication WO/2017/112828 A1, incorporated in its entirety herein, presents methods for encapsulating hydrophilic compounds in nanoparticles and microparticles. The methods include a description of a triblock copolymer stabilizer that could be used to form nanoparticles of the described structure. The present invention discloses enabling methods to employ the triblock copolymers to encapsulate hydrophilic compounds not previously envisioned in the prior art. It also discloses formulation parameters that can be central to controlling release from the nanoparticles formed by these processes, including an unexpected temperature dependence. These parameters are nonobvious given the current state of the art and enable tuning of release rates as required for the nanoparticle application.

Hydrophilic molecules such as biologics, which can include peptides, proteins, and other biologically-derived materials, can be used as therapeutic agents in medical applications. They can face administration challenges because of poor membrane permeability and rapid clearance from the blood stream. A variety of approaches can be taken to encapsulate soluble biologics to improve circulation time. Reported herein are methods for the formation of a core-shell-brush nanoparticle from an A-B-C triblock copolymer. A hydrophilic core can contain the biologic and the C Block of the copolymer. The shell can be comprised of the precipitated B Block, while the A Block can form a stabilizing brush layer. The particles can be assembled by sequential precipitations under defined mixing conditions. Tunable release of the biologic from the nanoparticles can be important in achieving the goals of a desired application. Presented herein are methods to tune release based on process parameters during particle assembly and triblock characteristics.

Encapsulation and delivery of soluble therapeutics and biologics, including peptides, proteins, DNA, and RNA, can be challenging. Biologics can exhibit poor stability, fast clearance times, immune recognition, and high costs. Nanoparticles, microparticles, and larger monoliths capable of releasing soluble therapeutics in a controlled manner that will protect them from degradation, clearance, and immune recognition are desired. Biologics are presently commonly delivered via injection, thus controlled release may reduce the frequency of drug administration and increase patient compliance.

Release of therapeutics from polymeric systems may be controlled in one of two ways. In the first method, the therapeutic is conjugated to the polymeric material of the scaffold. The therapeutic is released when it is cleaved from the scaffold. This is most commonly done with hydrogels. Because conjugation entails the formation of new chemical bonds, the system is subject to more rigorous FDA approval and is thus generally undesirable. In the second method, the soluble therapeutics are encapsulated within an insoluble but erodible matrix. The erodible matrices are hydrophobic and must be processed with hydrophobic organic solvents. Through this method chemical modification to the therapeutic can be avoided.

Flash NanoPrecipitation (FNP) is a previously patented process (U.S. Pat. No. 8,137,699 (herein, "'699 patent"), hereby incorporated by reference in its entirety herein) to make nanoparticles with a hydrophobic core and hydrophilic stabilizing shell (Johnson, B. K., et al., AIChE Journal (2003) 49:2264-2282). This process allows for the high loading of hydrophobic material and can reproducibly produce particles ranging in size from the micelle size of the stabilizing material up to several hundred nanometers. As set forth in two International Patent Application Publications, WO/2015/200054 and WO 2017/112828 A1, which are incorporated herein in their entirety, Flash NanoPrecipitation can be used to encapsulate biologics. Flash NanoPrecipitation technology can encapsulate biologics with high encapsulation efficiency and loadings greater than 75 wt %. These Publications describe a method for the formation of polymer-protected core-shell nanoparticles made by rapid precipitation, so that the resulting particles contain hydrophilic material in their core, and an organic-solvent soluble (less hydrophilic) shell. These nanoparticles having a hydrophilic core and a less hydrophilic shell can be termed "inverse" nanoparticles, in contrast with the nanoparticles of the '699 patent having a hydrophobic core and a hydrophilic shell.

The embodiments of the present invention offer methods to prepare the nanoparticles in the reforming solvent and to modify release and encapsulation efficiency from nanoparticles with a triblock copolymer stabilizer not previously envisioned. It was unexpected that lowering processing temperature would result in higher burst and faster release profiles. It was unexpected that the polymer molecular weight changes, loading variation, and the incorporation of specific lipid components would not modify release profiles, but that process solvents would result in differential kinetics.

Polymer Synthesis

An example A-B-C triblock copolymer that meets the requirements of the present disclosure is poly(ethylene glycol)-b-poly(lactic acid)-b-poly(aspartic acid), otherwise referred to as PEG-PLA-PAsp. This triblock copolymer can be synthesized through a sequential ring opening polymerization, starting with methoxy-poly(ethylene glycol)-hydroxyl (mPEG-OH). The PLA block can be grown from the hydroxyl end of the mPEG-OH through ring opening polymerization. For example, lactide monomer and a catalyst such as 4-(dimethylamino)pyridine (DMAP) can be added to fully dried mPEG-OH in with dry chloroform as the solvent, which will produce mPEG-PLA-OH. The polymer can be purified and recovered through precipitations in ice-cold methanol and isopropanol. After drying, the mPEG-PLA-OH can be converted to mPEG-PLA-$NH_2$, which can be used as an initiator for the PAsp polymerization. This can be achieved through a Steglich esterification with Boc-protected glycine (Boc-Gly). For example, the acid group of the Boc-Gly can be conjugated to the hydroxyl end of the mPEG-PLA-OH using N-(3-dimethylaminopropyl)-N'-ethylcarbodiimide hydrochloride with DMAP as a catalyst in dry chloroform. After the esterification is completed, the mPEG-PLA-Gly-Boc polymer is purified and recovered by precipitations in ice-cold isopropyl alcohol. Next, the Boc group can be removed in dry dichloromethane with trifluoroacetic acid, and the resulting mPEG-PLA-$NH_2$ polymer recovered by precipitations in cold diethyl ether. A desalting step may be required to convert the polymer end amine to the free-base form. Finally, the mPEG-PLA-$NH_2$ can be used as an initiator in the PAsp polymerization. For example, mPEG-PLA-$NH_2$ and β-Benzyl L-aspartic acid N-carboxyanhydride (Benzyl-Asp-NCA) can be stirred in dry chloroform to produce mPEG-PLA-PAsp(Benzyl), in which the PAsp acid groups are benzyl-protected. The benzyl protecting groups can be removed by adding concentrated HBr in acetic acid to the polymer solution in chloroform. The final mPEG-PLA-PAsp can be purified and recovered through precipitations in ice-cold diethyl ether. The PEG-PLA-PAsp A-B-C triblock copolymer produced using this method can be employed in the innovation described within this patent disclosure.

Nanoparticle Formation

Flash NanoPrecipitation Process

The Flash NanoPrecipitation (FNP) process can be used to create "inverse" particles with hydrophilic cores and/or with encapsulated water soluble agents, such as hydrophilic peptides. The process is illustrated in FIG. 1. A triblock copolymer 102 can be dissolved in a polar process solvent at a concentration of at least 0.1% by weight; the concentration of copolymer can be at least 0.2% by weight to form a first process solution. In an embodiment, the copolymer can be dissolved in the polar process solvent at a concentration in a range of from about 0.1 wt %, 0.2 wt %, 0.5 wt %, 1 wt %, 2 wt %, 5 wt %, 10 wt %, or 20 wt % to about 0.2 wt %, 0.5 wt %, 1 wt %, 2 wt %, 5 wt %, 10 wt %, 20 wt %, or 40 wt %. A person of skill in the art will appreciate that a factor such as the economics of a process can constrain a lower bound of concentration, and that factors such as the viscosity of the process solution or the solubility limit of the copolymer in the polar process solvent can constrain an upper bound of concentration. For example, if the viscosity of the first process solution is much greater than that of the nonprocess solvent, mixing of the first process solution with the nonprocess solvent may be inhibited. A person of skill in the art will appreciate that factors such as the molecular weight of the copolymer and the composition of the copolymer can affect the maximum concentration that can be attained in the polymer solution before the viscosity becomes too high.

Examples of copolymers include but are not limited to block copolymers, graft copolymers, and random copolymers that contain regions with different solvent solubilities within the same copolymer. For example, a poly(ethylene glycol)-b-poly(lactic acid)-b-poly(aspartic acid) (PEG-PLA-PAspA) copolymer can be used. Examples of process solvents include, but are not limited to, water, alcohols, acetone, acetonitrile, glycol ethers, dimethyl sulfoxide (DMSO), dimethylformamide, N-methyl-2-pyrrolidone, and mixtures thereof. The process solvent can be heated or pressurized or both to facilitate dissolution of the copolymer, depending on the dissolution characteristics of the copolymer in the solvent.

Upon micromixing the process solvent containing the copolymer with a less polar non-process solvent, such as chloroform, dichloromethane, or acetone, the dissimilar solubility characteristics of regions or portions of the copolymer are manifested and the more polar portions of the copolymer can no longer exist in the soluble state, so that an "inverse" nanoparticle 201 precipitates.

In an embodiment, additive water soluble target molecules 101, for example, a hydrophilic peptide, can be added to the copolymer 102 in the process solvent. Upon creation of nanoparticles 201 with the copolymer, the additive target molecule 101 will be incorporated in the nanoparticle. Additive target molecules 101 that are poorly soluble in the non-process solvent are coated, encapsulated, or confined as a particulate core and sterically stabilized by the protective colloid of the copolymer 102. The nanoparticles maintain a small and stable size in the nonprocess solvent.

In another embodiment, the target material and copolymer are dissolved in separate process solvent streams. The process solvent used to dissolve the copolymer and the process solvent used to dissolve the target material may be, but are not required to be, the same. For example, the target material (water soluble agent) can be dissolved in a first polar process solvent to form a water soluble agent solution, and the copolymer can be dissolved in a second polar process solvent to form a copolymer solution. These streams, the water soluble agent solution and the copolymer solution, are mixed, e.g., simultaneously mixed, with the nonprocess solvent to form a mixed solution. The first polar process solvent and the second polar process solvent can be miscible, or they can be completely miscible (i.e., so that another phase is not formed) at the volumetric ratios at which they are mixed. The first polar process solvent and the nonprocess solvent can be miscible, or they can be completely miscible (i.e., so that another phase is not formed) at the volumetric ratios at which they are mixed. The second polar process solvent and the nonprocess solvent can be miscible, or they can be completely miscible (i.e., so that another phase is not formed) at the volumetric ratios at which they are mixed. In another embodiment, the target material and copolymer are dissolved in a single process solvent stream. This stream is then rapidly mixed with a nonprocess solvent.

The intense micromixing of the process solution and the non-process solvent can be effected in several geometries. An idea is that high velocity inlet streams cause turbulent flow and mixing that occurs in a central cavity. The time for process solvent/non-process solvent mixing is more rapid than the assembly time of the nanoparticles. While not meant to be limiting, two such geometries have been previously described and analyzed: the Confined Impinging Jet mixer (CIJ) (Johnson, B. K., Prud'homme, R. K. Chemical processing and micromixing in confined impinging jets. *AIChE Journal* 2003, 49, 2264-2282; Liu, Y., Fox, R. O. CFD predictions for chemical processing in a confined impinging-jets reactor. *AIChE Journal* 2006, 52, 731-744) and the multi-inlet vortex mixer (MIVM) (Liu, Y., Cheng, C., Liu, Y., Prud'homme, R. K., Fox, R. O. Mixing in a multi-inlet vortex mixer (MIVM) for flash nano-precipitation. *Chemical Engineering Science* 2008, 63, 2829-2842). These examples are meant to be illustrative rather than limiting or exhaustive.

The fast mixing and high energy dissipation involved in this process provide mixing timescales that are shorter than the timescale for nucleation and growth of particles, which leads to the formation of nanoparticles with active agent loading contents and size distributions not provided by other technologies. When forming the nanoparticles via Flash NanoPrecipitation, mixing occurs fast enough to allow high supersaturation levels, for example, as high as 10,000, of all components to be reached prior to the onset of aggregation. The supersaturation level is the ratio of the actual concentration of a material, for example, a copolymer, in a solvent to the saturation concentration of that material in that solvent. For example, the supersaturation levels can be at least about 1, 3, 10, 30, 100, 300, 1000, or 3000 and can be at most about 3, 10, 30, 100, 300, 1000, 3000, 10,000, 30,000, or 100,000. The timescales of aggregation of the target material and copolymer self-assembly are balanced. Therefore, the target material and polymers precipitate simultaneously, and overcome the limitations of low active agent incorporations and aggregation found with the widely used techniques based on slow solvent exchange (e.g., dialysis). The Flash NanoPrecipitation process is insensitive to the chemical specificity of the components, making it a universal nanoparticle formation technique.

The size of the resulting nanoparticles from this process can be controlled by controlling the mixing velocity used to create them, the total mass concentration of the copolymer and target molecules in the process solvent, the process and non-process solvents, the ratio of the copolymer and target molecule, and the supersaturation of the target molecule and non-soluble portion of the copolymer upon mixing with the non-process solvent.

Nanoparticles can be produced from copolymers that are dissolved in a process solvent with no target material added.

Using the methods according to the invention, particles can be made that have sizes in the range of 15 nm to 10500 nm, sizes in the range of 20 nm to 6000 nm, sizes in the range of 20 nm to 1000 nm, sizes in the range of 35 nm to 400 nm, or sizes in the range of 40 nm to 300 nm. Sizes can be determined by dynamic light scattering. For example, particles can be made that have sizes of at least about 15 nm, 20 nm, 35 nm, 40 nm, 50 nm, 100 nm, 200 nm, 300 nm, 400 nm, 600 nm, 900 nm, 1000 nm, 2000 nm, 4000 nm, or 6000 nm, and have sizes of at most about 20 nm, 35 nm, 40 nm, 50 nm, 100 nm, 200 nm, 300 nm, 400 nm, 600 nm, 900 nm, 1000 nm, 2000 nm, 4000 nm, 6000 nm, or 10500 nm. Sizes reported and cited herein are the intensity average reported values as determined by the Malvern Nanosizer deconvolution program for particles smaller than 2000 nm, and determined by scanning electron micrcoscopy, or optical microscopy and image analysis using Image J for sizes greater than 2000 nm. Other intensity weighted deconvolution methods can be used to determine sizes of the nanoparticles.

Encapsulated Material

Encapsulated material (target molecules) must be sufficiently polar that it rapidly precipitates in the less polar non-process solvent. Molecules that do not meet these criteria may be chemically modified to increase their water solubility and propensity to precipitate in the organic non-process solvent. Examples of biologic material that may be encapsulated include, but are not limited to, peptides, proteins, DNA, RNA, saccharides, and derivatives, conjugates, and/or analogs thereof. Small molecule water soluble therapeutics and imaging agents may also be encapsulated. Soluble stabilizing agents may be encapsulated in particles to provide stability to the particle for its use or for subsequent processing steps. Any of these materials may also be co-precipitated within a single particle. Hydrophilic material may be encapsulated for the sole purpose of adding stability to the particles during post processing. For example, material with molecular weights between 100 and 10,000,000 Daltons (Da) may be encapsulated. Material with molecular weights between 250 and 10,000,000 Da may be encapsulated. Material with molecular weights between 100 and 1,000,000 Da may be encapsulated. Material with molecular weights between 250 and 1,000,000 Da may be encapsulated. Material with molecular weights between 100 and 200,000 Da may be encapsulated.

Certain encapsulated materials may be multifunctional. For example, tobramycin is cationic and can itself be cross-linked with a copolymer. Other cationic active materials, with multiple cationic residues will similarly crosslink the anionic polymer blocks.

The encapsulated material may be incorporated into the particle at a range of loadings. For example, the mass of the encapsulated material may be greater than or equal to the mass of the copolymer. For example, the concentration of the encapsulated material in the first process solution may be from about 0.1 wt %, 0.2 wt %, 0.5 wt %, 1 wt %, 2 wt %, 5 wt %, 10 wt %, or 20 wt % to about 0.2 wt %, 0.5 wt %, 1 wt %, 2 wt %, 5 wt %, 10 wt %, 20 wt %, or 40 wt %.

Solvents

Formation of nanoparticles requires one or more process solvents and one or more non-process solvent streams. The process and non-process solvents may be a pure (that is, a single) liquid compound or a mixture of two or more pure liquid compounds. Other non-liquid compounds that aid in the solvent quality of the streams may be added and are also considered part of the solvent. For example, a surfactant, a salt, or a cosolvent may be added to a solvent and considered part of the solvent. These excipient compounds may or may not be in the final nanoparticle or microparticle construct, depending on the requirements of the final product.

The polar process solvent containing the copolymer is chosen such that the copolymer is molecularly dissolved. This requires that the process solvent solubilize all parts of the copolymer. The process solvent containing the material to be encapsulated, if present, is also chosen such that material is molecularly dissolved. These process solvents may be, but are not required to be, the same. In some cases, both the copolymer and material to be encapsulated may be dissolved in a single solution of the process solvent. In order to dissolve the water soluble material to be encapsulated, the process solvent is more polar than the non-process solvent. Examples of process solvents include, but are not limited to, water, alcohols, methanol, ethanol, glycol ethers, dimethyl formamide (DMF), dimethyl sulfoxide (DMSO), acetonitrile, acetone, N-methyl pyrrolidone (NMP), and mixtures thereof. Acids, bases, and salts are a few examples of additives that may be used to aid in the solubilization of the copolymer and encapsulated material in the process solvent.

The solutions of process solvent containing copolymer and material to be encapsulated are mixed with a nonprocess solvent. The non-process solvent must be capable of changing the local molecular environment of the copolymer and causing local precipitation of the C Block of the polymer. The nonprocess solvent is chosen such that the more polar sections of the copolymer rapidly precipitate and Blocks B & A of the copolymer remain solubilized. Thus, the copolymer will self-assemble into the desired nanoparticle form in the nonprocess solvent. The nonprocess solvent is chosen such that the target material to be encapsulated rapidly precipitates in the final mixture. The process and non-process solvents can be fully miscible at the final composition. In some cases, no more than 20 volume percent of the process solvent may phase separate in the final composition. In general, this is only acceptable if the phase separated solvent goes to the core of the particles and there is no macroscopic separation. Non-process solvents include, but are not limited to, chloroform, dichloromethane, alkanes such as hexane, ethers such as diethyl ether, tetrahydrofuran (THF), toluene, acetone, and mixtures thereof. Acids, bases, and salts are a few examples of additives that may be used to aid in the precipitation of the encapsulated material and sections of the copolymer. Solvent choices are made based on the solubilities of the copolymer and encapsulated materials. It is important to note that process solvents of one system may work well as the nonprocess solvent in another system, thus the examples given above for process and nonprocess solvents should not be considered distinct.

Copolymers

The stabilizing polymer can be a copolymer of a more polar block that is not soluble in the nonprocess solvent (Block C), coupled with a more nonpolar (less polar) block that is not soluble in the reforming solvent (Block B), coupled with a distinct block that is soluble in the nonprocess solvent and the reforming solvent (Block A). The term "block" may be interpreted as either a distinct domain with a single molecular composition, or it may mean a region of the polymer chain which has regions that are predominantly more polar and other regions that are less polar. The polarity may be imparted by the monomers comprising the polymer backbone or grafted pendant groups or chains attached to the main polymer backbone. For example, the copolymer may be amphiphilic (the more nonpolar block is not water soluble), however, this is not a requirement and copolymers may be fully water soluble or fully non-water soluble, as long as solubilities of the blocks differ significantly enough in the nonprocess solvent. The copolymer should self-assemble in the nonprocess solvent, with the more polar Block C precipitating and the more nonpolar blocks remaining soluble. When used in the FNP process to make particles, the more polar Block C goes to the core of the particle, and the more nonpolar Blocks B & A form a sterically protective shell. The sterically protective shell prevents particle aggregation and prevents percolation of encapsulated material during post processing steps.

Nanoparticles formed by the disclosed process can be formed with graft, block, or random copolymers. For example, these copolymers can have a molecular weight between about 1000 g/mole and about 1,000,000 g/mole, or between about 3000 g/mole and about 25,000 g/mole, or at least about 2000 g/mole.

The copolymers are comprised of repeat units or blocks that have different solubility characteristics. Typically, these repeat units are in groups of at least two comprising a block of a given character. Depending on the method of synthesis, these blocks could be of all the same repeat unit or contain different repeat units dispersed throughout the block, but still yielding blocks of the copolymer with polar and more non-polar portions. For example, Block B could be comprised of glycolic acid and lactic acid monomer residues (PLGA).

These blocks can be arranged into a series of three blocks (triblock) or more (multiblock), forming the backbone of a block copolymer. In addition, the polymer chain can have chemical moieties covalently attached or grafted to the backbone. Such polymers are graft polymers. Block units making up the copolymer can occur in regular intervals or they can occur randomly making a random copolymer. In addition, grafted side chains can occur at regular intervals along the polymer backbone or randomly making a randomly grafted copolymer. In graft polymers, polar blocks may be grafted on a non-polar polymer. Non-polar blocks may be grafted on a more polar polymer chain. In graft copolymers, the length of a grafted moiety can vary. The grafted segments can be equivalent to 2 to 22 ethylene units in length. The grafted hydrophobic groups which create at least one less polar region of the copolymer may comprise tocopherol, tocopherol derivatives, lipids, alcohols with carbon numbers from 12 to 40, cholesterols, unsaturated and/or hydrogenated fatty acids, salts, esters or amides thereof, fatty acids mono-, di- or triglycerides, waxes, ceramides, cholesterol derivatives, or combinations. In addition, the grafting of the polymer backbone can be useful to enhance solvation or nanoparticle stabilization properties.

The copolymer used in the compositions and methods of the invention may be comprised of blocks of at least two repeat units or with a minimum contour length the equivalent of at least 25 ethylene units. Contour lengths are the linear sum of the polymer backbone, the molecular dimensions of which can be approximated using the Polymer Handbook, 4th Edition, eds. J. Brandrup, E. H. Immergut, and E. A. Grulke, assoc. ed. A. Abe, D. R. Bloch, 1999, New York, John Wiley & Sons, which is hereby incorporated by reference in its entirety.

Examples of suitable nonpolar Block B in a copolymer include but are not limited to the following: acrylates including methyl acrylate, ethyl acrylate, propyl acrylate, n-butyl acrylate (BA), isobutyl acrylate, 2-ethyl acrylate, and t-butyl acrylate; methacrylates including ethyl methacrylate, n-butyl methacrylate, and isobutyl methacrylate; acrylonitriles; methacrylonitrile; vinyls including vinyl acetate, vinylversatate, vinylpropionate, vinylformamide, vinylacetamide, vinylpyridines, vinyl phenols and vinyllimidazole; aminoalkyls including aminoalkylacrylates, aminoalkylsmethacrylates, and aminoalkyl(meth)acrylamides; styrenes; cellulose acetate phthalate, cellulose acetate succinate, hydroxypropylmethylcellulose phthalate, poly(D,L-lactide), poly (D,L-lactide-co-glycolide), poly(glycolide), poly(hydroxybutyrate), poly(alkylcarbonate) and poly(orthoesters), polyesters, poly(hydroxyvaleric acid), polydioxanone, poly(ethylene terephthalate), poly(malic acid), poly(tartronic acid), polyanhydrides, polyphosphazenes, poly(amino acids), lactic acid, caprolactone, glycolic acid, and their copolymers (see generally, Illum, L., Davids, S. S. (eds.) Polymers in Controlled Drug Delivery Wright, Bristol, 1987; Arshady, J. Controlled Release 17:1-22, 1991; Pitt, Int. J. Phar. 59:173-196, 1990; Holland et al., J. Controlled Release 4:155-0180, 1986); hydrophobic peptide-based polymers and copolymers based on poly(L-amino acids) (Lavasanifar, A., it al., Advanced Drug Delivery Reviews (2002) 54:169-190), poly(ethylene-vinyl acetate) ("EVA") copolymers, silicone rubber, polyethylene, polypropylene, polydienes (polybutadiene, polyisoprene and hydrogenated forms of these polymers), maleic anhydride copolymers of vinyl methylether and other vinyl ethers, polyamides (nylon 6,6), polyurethane, poly(ester urethanes), poly(ether urethanes), poly(esterurea). For example, polymeric blocks can include poly(ethylenevinyl acetate), poly(D,L-lactic acid) oligomers and polymers, poly(L-lactic acid) oligomers and polymers, poly(glycolic acid), copolymers of lactic acid and glycolic acid, poly(caprolactone), poly(valerolactone), poly-anhydrides, copolymers of poly(caprolactone) or poly(lactic acid), or poly(propylene sulfide). For certain applications, e.g., non-biologically related applications, polymeric blocks can include, for example, polystyrene, polyacrylates, and butadienes.

Natural products with sufficient hydrophobicity to act as the non-polar portion of the polymer include: hydrophobic vitamins (for example vitamin E, vitamin K, and vitamin A), carotenoids, and retinols (for example, beta carotene, astaxanthin, trans and cis retinal, retinoic acid, folic acid, dihydrofolate, retinylacetate, retinyl palmintate), cholecalciferol, calcitriol, hydroxycholecalciferol, ergocalciferol, alpha-tocopherol, alpha-tocopherol acetate, alphatocopherol nicotinate, estradiol, lipids, alcohols with carbon numbers from 12 to 40, cholesterols, unsaturated and/or hydrogenated fatty acids, salts, esters or amides thereof, fatty acids mono-, di- or triglycerids, waxes, ceramides, cholesterol derivatives or mixtures thereof. For example, a natural product is vitamin E which can be readily obtained as a vitamin E succinate, which facilitates functionalization to amines and hydroxyls on the active species.

A suitable polar Block C is a region insoluble in the nonprocess solvent. The following maybe used or used in combinations, and includes but is not limited to the following: carboxylic acids including acrylic acid, methacrylic acid, itaconic acid, and maleic acid; polyoxyethylenes or polyethylene oxide; polyacrylamides and copolymers thereof with dimethyl-aminoethyl-methacrylate, diallyl-dimethyl-ammonium chloride, vinylbenzyl trimethylammonium chloride, acrylic acid, methacrylic acid, 2-acryamideo-2-methylpropane sulfonic acid and styrene sulfonate, polyvinyl pyrrolidone, starches and starch derivatives, dextran and dextran derivatives; polypeptides, such as polylysines, polyarginines, polyaspartic acids, polyglutamic acids; poly hyaluronic acids, alginic acids, polylactides, polyethyleneimines, polyionenes, polyacrylic acids, and polyiminocarboxylates, gelatin, and unsaturated ethylenic mono or dicarboxylic acids. To prepare anionic copolymers, acrylic acid, methacrylic acid, poly(glutamic acid) and/or poly aspartic acid polymers can be used. To produce cationic copolymers, DMAEMA (dimethyl aminoethyl methacrylate), polyvinyl pyridine (PVP), and/or dimethyl aminoethyl acrylamide (DMAMAM) can be used. A listing of suitable polar, water soluble, polymers can be found in Handbook of Water-Soluble Gums and Resins, R. Davidson, McGraw-Hill (1980).

The lists above of nonpolar and polar polymers should not be considered exclusive of one another. Copolymers of two polymers given in a single list may have sufficient differences in solubilities in a given nonprocess solvent to be used in this process.

Examples of a suitable Block A include polyoxyethylenes, poly(ethylene glycol), poly(propylene oxide), polysaccharides, poly(vinyl alcohol), polypeptides, polyvinyl pyrrolidone, starches and starch derivatives, dextran and dextran derivatives, gelatin, DMAEMA (dimethyl aminoethyl methacrylate), polyvinyl pyridine (PVP), and/or dimethyl aminoethyl acrylamide (DMAMAM), poly(N-(2-Hydroxypropyl) methacrylamide), or combinations.

For example, block A can have a molecular weight ranging from about 0.1 kDa, 0.5 kDa, 1 kDa, 2 kDa, or 5 kDa to about 5 kDa, 10 kDa, 20 kDa, 50 kDa, 100 kDa, or 200 kDa. For example, block B can have a molecular weight ranging from about 0.2 kDa, 0.5 kDa, 1 kDa, 2 kDa, 5 kDa, 10 kDa, or 20 kDa to about 10 kDa, 20 kDa, 40 kDa, 100 kDa, 200 kDa, or 400 kDa. For example, block C can have a molecular weight ranging from about 0.1 kDa, 0.5 kDa, 1 kDa, 2 kDa, or 5 kDa to about 5 kDa, 10 kDa, 20 kDa, 50 kDa, 100 kDa, or 200 kDa.

For example, a triblock copolymer can have block A as poly(ethylene glycol) (PEG), block B as poly(lactic acid) (PLA), and block C as poly(aspartic acid) (PAsp), that is, PEG-b-PLA-b-PAsp.

Nanoparticle Processing

Particle Stabilization

The particles are formed and stable in the organic nonprocess solvent. For most applications, it can be required that the final construct be stable in aqueous environments for a set, nonnegligible amount of time. In order to process the particles into an aqueous environment, particle stabilization is required. Without stabilization, the particle may dissolve, aggregate, and/or release the water soluble target material from the core.

In an embodiment according to the invention, sections of the core of the particle may be stabilized. The core refers to Block C of the copolymer and encapsulated material. Material may be incorporated into the core specifically for the purpose of particle stabilization. For example, the portions of the copolymer in the core may be crosslinked to form a particle with a crosslinked core. In another embodiment, the shell of the particle may be stabilized. The shell refers to Block B of the copolymer that is soluble in the nonprocess solvent.

Stabilization can involve the formation of new covalent bonds. For example, the copolymer of the core (and, in some cases, the encapsulated material) of the particle may be cross-linked through the formation of new covalent bonds. The bonds may be formed directly between groups on the copolymer. Covalent bonds may be formed by adding a crosslinking material to the core for the specific purpose of cross-linking the polymer in the core. The crosslinking material (stabilizing material) may be added to the core of the particle during the FNP process. For example, the crosslinking material can be included in the process solvent. As another example, the crosslinking material can be included in the nonprocess solvent.

Alternatively, the crosslinking material may be added to the solution after the particle has formed. For example, the particle may be "incubated" with a crosslinking material, such as a metal salt, and the crosslinking material may interact with Block C of the copolymer, e.g., PAA, for example, through ionic and/or chelation effects. The degree of crosslinking realized can then be characterized by suspending the particle in a good solvent for the more polar portion of the copolymer. Particles with tight (dense) crosslinking can exhibit minimal swelling and can be associated with high levels of metal partitioning into the hydrophilic core and strong metal interactions with the more polar part of the polymer. Particles with loose crosslinking can exhibit high levels of swelling and can be associated with low levels of metal partitioning into the hydrophilic core and weak metal interactions with the more polar part of the polymer. If the partitioning of the metal into the core is very low and or the interaction of the metal with the more polar part of the polymer is very weak, then the particle may disassemble and dissolve in the solvent.

If the crosslinking material is added after the particles have been formed, the crosslinking may be diffusion limited and only occur on the outer layers of the core. If the crosslinking material is added to the solution after the particles have been formed, the particle may be cross-linked throughout the core if the core is swollen with solvent or if the cross-linking material is small enough to diffuse throughout the core. The shell of the particle may be cross-linked through the formation of new covalent bonds. The bonds may be formed directly between groups on the copolymer, or through the addition of an extra crosslinking material.

Examples of covalent chemistries that may be used include, but are not limited to carbodiimide coupling of carboxylic acids to alcohols or carboxylic acids to amines, the coupling of activated esters to alcohols or amines, maleimide-thiol chemistry, Michael addition, azide-alkyne "click" chemistry, UV or light activated chemistries, and/or disulfide formation.

Stabilization can be obtained through non-covalent interactions. The core of the particle may be cross-linked through non-covalent interactions. The interactions may be directly between groups on the copolymer. Non-covalent interactions may be formed by adding a crosslinking material to the core for the specific purpose of cross-linking the polymer in the core. This crosslinking material may be added to the core of the particle during the FNP process. Alternatively, this crosslinking material may be added to the solution after the particle has formed. If the crosslinking material is added after the particles have been formed, the crosslinking may be diffusion limited and only occur on the outer layers of the core. If the crosslinking material is added to the solution after the particles have been formed, the particle may be crosslinked throughout the core if the core is swollen with solvent or if the crosslinking material is small enough to diffuse throughout the core. The shell of the particle may be cross-linked through noncovalent interactions. The interactions may be formed directly between groups on the copolymer, or through the addition of an extra crosslinking material.

Examples of non-covalent interactions that may be used include, but are not limited to, ionic interactions, acid-base interactions, metal chelation, interactions between polyhistidines and a metal such as nickel, and/or strong hydrogen bonding. An example of non-covalent particle stabilization is the use of Cr(III) to stabilize the poly(acrylic acid) core of a nanoparticle. For example, chromium (III) acetate and/or chromium (III) bromide can be used as crosslinking materials. The crosslinking may proceed through ligand exchange. The solvents used can act as ligands. For example, the interaction of the cation in a crosslinking salt should be stronger with the more polar portion of the copolymer to be crosslinked in the core than with the anion in the salt.

Other crosslinking materials (crosslinking agents) that can be used to induce non-covalent crosslinking include alkaline earth halides, magnesium halides, calcium halides, zinc halides, metal halides, transition metal halides, and iron halides. Metal salts can be used. Additional crosslinking materials that can be used are metal nitrates, metal acetates, alkaline earth acetates, transition metal acetates, and calcium acetate. The crosslinking ability of a given cation (e.g., a metal) depends on the accompanying anion. The crosslinking ability of a crosslinking material, e.g., a salt, can depend on the process solvent and nonprocess solvent used. A crosslinking material can include a metal that is biological interesting or functional or otherwise useful. For example, Fe(III), Ca(II), and Zn(II) cations are biocompatible. Gd(III) (gadolinium(III)) is active in magnetic resonance imaging (MRD, and, therefore, can be useful as a tracer.

Some crosslinking materials that work well when conducting crosslinking during nanoparticle formation, e.g., during the FNP process, include polyamines, such as spermine or tetraethylene pentamine, and certain chloride salts, such as magnesium chloride, calcium chloride, and iron(III) chloride. For example, such crosslinking materials can be used with PBA-b-PAA copolymer, methanol, dimethylsulfoxide, and/or water as the process solvent, and acetone and/or chloroform as the nonprocess solvent. It may be necessary to include some water in the process solvent for the crosslinking to occur. For example, 2.5 vol % or 5 vol % or 10 vol % water in process solvent such as DMSO. In some systems, calcium chloride, magnesium chloride, and spermine may act as weak crosslinkers. An iron(III) salt, such as iron(III) chloride, may induce strong crosslinking.

Multiple types of stabilization chemistries may be employed within a given particle. Stabilization may occur in the core, in the shell, at the interface, or in multiple locations within a given particle.

For many applications, particle degradation and release of encapsulated material is required. The type of stabilization chemistry used, and the density of the crosslinked network, may affect the degradation kinetics of the particle. The type of stabilization chemistry used, and the density of the cross-linked network, may also or alternatively affect the release kinetics of encapsulated material from the core of the particle.

For some applications, it is required that the encapsulated material is not chemically modified. In these cases, non-covalent interactions should be used to stabilize the particle. However, covalent crosslinking may be used as long as the chemistry is specific to the copolymer and does not modify the encapsulated material.

In certain cases, the addition of a pH modifying agent (e.g. an acid or a base) can strengthen crosslinking by promoting ionic interactions between the crosslinker and Block C of the stabilizer. The acid or base may be added during particle assembly or after particle assembly to the nonprocess solution. For example, ammonia at 0.6 equivalents with respect to the moles of acid side chains in Block C can be added to the nanoparticle solution with stirring. The solution can then be incubated to allow for crosslinking to occur. The ammonia is first diluted in methanol due to the low volume requirements. Without being limited by theory, base addition promotes deprotonation of the acid groups to enable ionic interactions with the metal cation.

Nanoparticle Reforming Process

Figure 3:
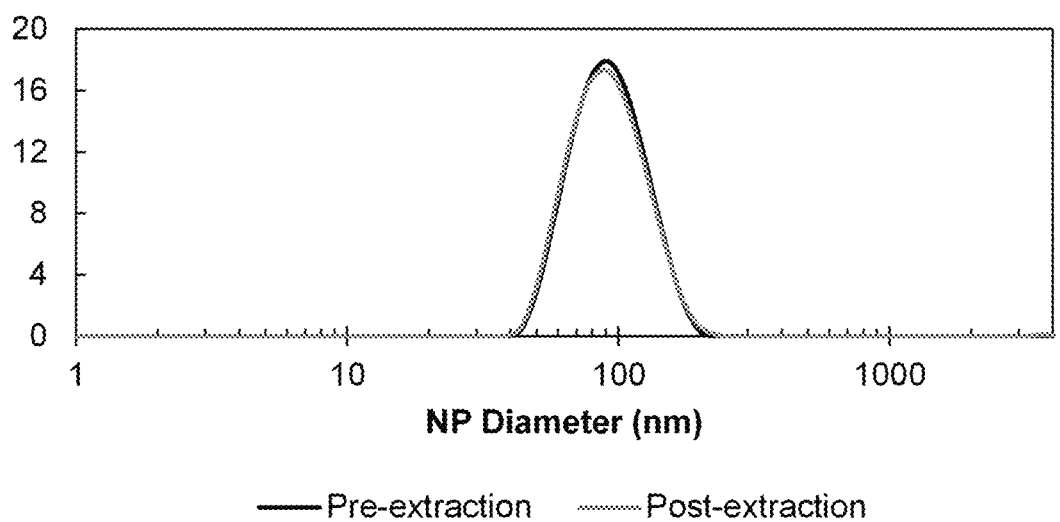
FIG. 3 shows the size stability of a triblock-coated inverse nanoparticle (NP) in an extraction with 160 mM phosphate-buffered saline by DLS analysis. The samples were prepared according to Example 1 with vancomycin as the encapsulated material.

Transfer of the nanoparticles to a reforming solvent can result in precipitation of Block B of the stabilizer while Block A remains as a stabilizing brush. Collapse of this block imparts controlled release of the encapsulated biologic, as well as enhanced protection from degradation by mechanisms within the human body. Employing a triblock copolymer stabilizer provides an elegant way to install the stabilizing polymer brush. Use of two different diblock copolymers, as described in International Patent Application Publications WO/2015/200054 and WO 2017/112828 A1, can lead to the formation of empty nanoparticles of the second block copolymer stabilizer. A triblock copolymer is "pre-localized" to the individual particle surface to increase the local concentration of stabilizer and produce narrower size distributions, as demonstrated (shown) in FIG. 2.

Most applications of biologics encapsulated in nanoparticles require their dispersion in an aqueous environment. Water can serve as a reforming solvent for the precipitation of Block B. Alternatively, other polar solvents such as alcohols, can serve as reforming solvents. In this case, encapsulation efficiency may be improved by forming the hydrophobic shell around each nanoparticle core prior to transfer to an aqueous environment which solubilizes the encapsulated biologic. The present invention discloses novel methods of Block B precipitation using reforming solvents.

If the reforming solvent is to be water or an aqueous solution but the nonprocess solvent for the inverse nanoparticles is not miscible in water, the nanoparticles must first be exchanged into a second miscible nonprocess solvent. In some cases, this may be accomplished by centrifugation to remove the nanoparticles from suspension, decanting of the first nonprocess solvent, and resuspension in the second nonprocess solvent. If the first nonprocess solvent has a high density (such as DCM or chloroform), it may be necessary to first add a low density nonprocess solvent to enable successful centrifugation.

In other cases, solvent exchange can be completed by distillation. This unit operation has a number of variables: concentration, vacuum pressure, and jacket temperature, for example. One skilled in the art would recognize that a number of conditions are possible to achieve the stated goal of solvent exchange. Methods commonly used in the pharmaceutical industry such as put-and-take distillation or constant-volume distillation can be used. Commonly, a put-and-take distillation is employed where the solution is first diluted with an equal volume of the second nonprocess solvent (which is miscible with the reforming solvent). The put-and-take cycle then consists of concentration to, e.g., 2, 4, 5, 7.5, 10, 12, 15, 20, 30, or 40 mg/ml based on the total nanoparticle concentration (mass of encapsulated material and polymer, less any process losses). One skilled in the art would recognize that a number of process constraints such as working volumes or stability can dictate this target composition. The concentrated solution is then diluted to, e.g., 0.01, 0.05, 0.1, 0.5, 1, or 2 mg/ml with the second nonprocess solvent. This is repeated, for example, anywhere from 3 to 4 to 5 or to 10 times. The final composition must be such that the solution after solvent exchange remains completely miscible with the reforming solvent. That is, that the residual first nonprocess solvent is below the concentration where phase separation would occur in the final solution with the reforming solvent. The final nanoparticle concentration can be, for example, 0.5 mg/ml, or 1 mg/ml, or 2 mg/ml or 5 mg/ml or 7.5 mg/ml or 10 mg/ml, 15 mg/ml, 20 mg/ml, or 50 mg/ml as dictated by system stability or downstream process requirements.

In some cases, the first polar solvent or solvent combination is not volatile under the conditions of the distillation. That is, the polar solvent will be preferentially retained with the nanoparticle solution. If this can lead to disruption of the nanoparticles (e.g., through solubilization of the core components), then the polar solvent must be removed prior to distillation. This can be achieved by solvent extraction using an aqueous solution as reported by Markwalter & Prud'homme and incorporated in its entirety herein (Inverse Flash NanoPrecipitation for Biologics Encapsulation: Understanding Process Losses via an Extraction Protocol. C. E. Markwalter and R. K. Prud'homme. *Control of Amphiphile Self-Assembling at the Molecular Level: Supra Molecular Assemblies with Tuned Physicochemical Properties for Delivery Applications*. Jan. 1, 2017, 275-296). This method was previously only applied to nanoparticles in a nonprocess solvent that contained a single hydrophobic block in the stabilizing brush. The steric stabilization from this brush can also work to reduce any preference of the nanoparticle for the interface in the extraction. It was surprising that nanoparticles containing a stabilizing brush with both Block B and Block A could be processed in an aqueous extraction, where in certain embodiments Block A may be soluble in both the nonprocess solvent and water. For example, Block A may be PEG (polyethylene glycol), which exhibits solubility in many organic solvents as well as water. One skilled in the art would have expected that processing a nanoparticle solution in the extraction might be infeasible if the nanoparticles helped to stabilize an emulsion which could not be readily separated at the completion of the unit operation. The inherent size stability is demonstrated in FIG. 3.

The aqueous phase of the extraction can be or include a 150 mM sodium chloride solution in water which is added to the nonprocess solution containing the nanoparticles. Alternative conditions can include no sodium chloride or high sodium chloride concentrations up to the saturation limit in water. Other alternative conditions can include an aqueous buffer or other components to reduce encapsulated biologic solubility in the aqueous phase. The biphasic mixture is contacted for 20 minutes or 30 minutes or 60 minutes or up to 120 minutes. The two solutions can then be separated by methods familiar to those skilled in the art and the nonprocess solution of nanoparticles retained for further processing. The purpose of adding a salt to the extraction brine phase is to approximately equalize the osmotic pressure of the brine with the osmotic pressure arising from the biologic and Block C components in the core. If the extraction brine has too low of an osmotic pressure, then water from the aqueous extraction phase will partition into the core of the nanoparticle and swell and then destabilize the nanoparticle.

Figure 4:
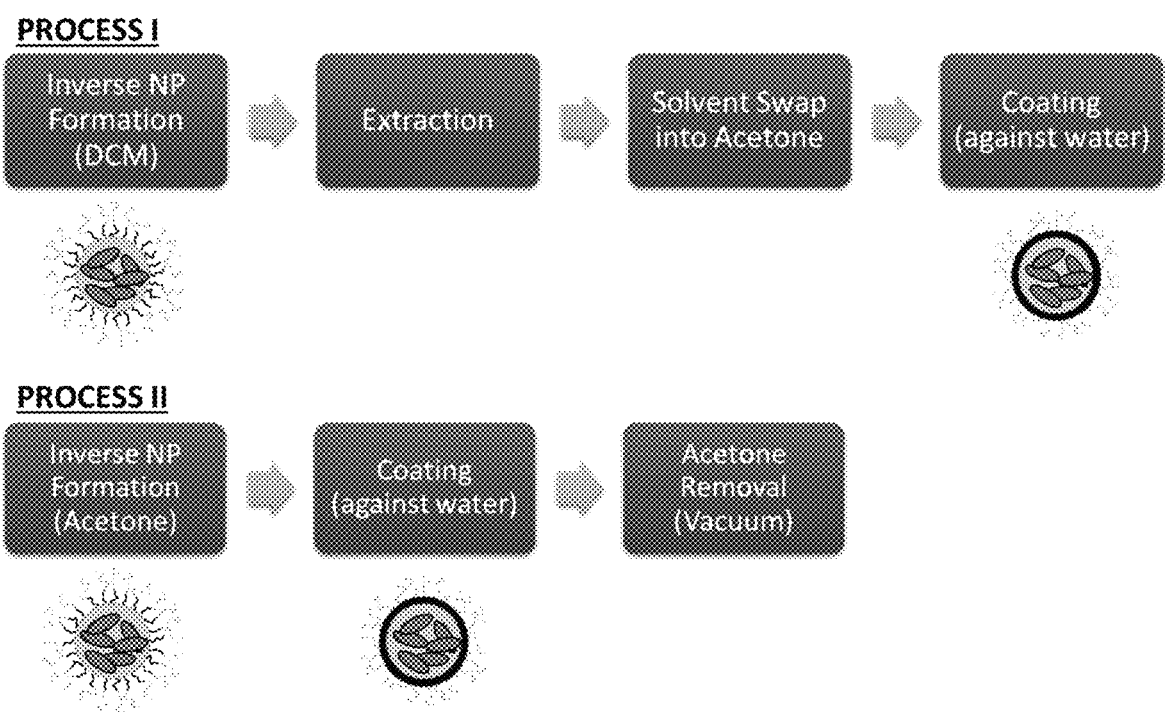
FIG. 4 depicts the order of unit operations for Process 1 (I) and Process 2 (II) as well as the process step where particle architecture changes due to Block B collapse.

Following the extraction and then the solvent swap to a second nonprocess solution, the nanoparticles can be mixed with the reforming solvent. This results in the precipitation of Block B. In some embodiments, the mixing can be by simply contacting the two phases with gentle agitation. In some embodiments, the mixing can be carried out to achieve rapid micromixing of the second nonprocess solvent and the reforming solvent. This can be in a confined impinging jet (CIJ) mixer or in a multi-inlet vortex mixer or any mixer that one skilled in the art recognizes is sufficient to achieve the desired result. In a MIVM, different flow ratios of the reforming solvent and the nanoparticle solution can directly result in a target final concentration of the second nonprocess solvent as noted below. In a CIJ mixer, the second nonprocess solvent solution is mixed against an equal volume of the reforming solvent. The mixture can be diluted further with reforming solvent after initial mixing. The final concentration of the second nonprocess solvent can be 50 vol %, 40 vol %, 30 vol %, 20 vol %, 10 vol %, 5 vol %, or 1 vol %. One skilled in the art would recognize that the solvent composition should be chosen such that Block B has precipitated, but within economic constraints for the process. The process of extraction, solvent exchange, and reforming is referenced herein as "Process 1 (I)" for brevity and is depicted in FIG. 4.

Examples of suitable reforming solvents include water, aqueous solutions of salt, aqueous solutions or salt and buffer components, 150 mM sodium chloride in water, phosphate buffered saline, methanol, ethanol, alcohols. A suitable reforming solvent is a poor solvent for the Block B of the stabilizing polymer, but is a good solvent for Block A. In process design, a suitable reforming solvent for some stabilizing polymers may be a nonprocess solvent for other stabilizers.

In a variation of Process 1 (I), the reforming solvent can replace a second nonprocess solvent in the solvent exchange. For example, an alcohol can be used such that the result is the precipitation of Block B during the solvent exchange. The nanoparticle dispersion in alcohol may then be diluted into water or release buffer as described below and if required by the application. Under some combinations of process condition and Block A identity, the nanoparticles may aggregate. They may then be concentrated by centrifugation or filtration and redispersed in aqueous solution as described in Example 5.

If the first nonprocess solvent is miscible with the reforming solvent (e.g. water), then the nanoparticle solution can be directly mixed with the reforming solvent. The mixing process may be such that rapid micromixing is achieved. This may be accomplished with any appropriate mixer known to those skilled in the art. For example, the mixing can be carried out in a CIJ mixer or a MIVM, as described above. In some embodiments, the mixing process may be carried out with simple gentle mixing. The mixing may be carried out at low temperature or at ambient temperature, the lower temperature bound being dictated by the nonprocess solvent and the reforming solvent properties. For example, the two streams to be mixed can be cooled to 0° C. to 5° C. on wet ice. The relative volume of the reforming solvent can be 20%, 30%, 40%, 50%, 60%, 70%, 80%, 90%, or higher. For example, the ratio of the nonprocess solvent to the reforming solvent can be 1:1, or 1:2, or 1:3, or 1:5, or 1:10, or 1:20, or 1:0.5. One skilled in the art would recognize that vessel volumes and process economics will constrain these choices and that the solvent conditions selected must result in the precipitation of Block B. In one method of the invention, a nanoparticle solution in acetone as a nonprocess solvent can be mixed with an equal volume of water as a reforming solvent. In one embodiment, the mixing can be done after cooling the solutions on wet ice. In a second embodiment, the mixing can be at ambient conditions. In one method of the invention, the mixing can be done by adding the water to the acetone solution at about 5 ml/min. In one method of the invention, the water is added by rapid mixing in a CIJ.

The residual nonprocess solvent may be removed by several means to further vitrify Block B. If the nonprocess solvent has a lower boiling point than the reforming solvent, the nonprocess solvent may be preferentially removed by evaporative distillation. One skilled in the art will recognize that process conditions will depend upon the solvent composition of a particular application. In certain cases, the required conditions will not be accessible within the stability bounds for the nanoparticle or the encapsulated biologic. For example, a 1:1 mixture of acetone and water (nonprocess solvent and reforming solvent respectively) can be subjected to evaporative distillation to preferentially remove acetone. In one embodiment, the distillation can be carried out at a jacket temperature of 0° C. with vacuum at 40 mbar. In another embodiment, the distillation can be carried out a jacket temperature of 20° C. with a vacuum pressure of 70 mbar. Thermodynamic constraints dictate that the complete removal of residual nonprocess solvent is not achievable. Sufficient nonprocess solvent removal is achieved when the downstream processing steps are feasible. This might indicate residual nonprocess solvent of 10 vol %, 7.5 vol %, 5 vol %, 2.5 vol %, 1 vol %, or lower. For simplicity, the direct mixing of the nonprocess solvent solution with a reforming solvent will be referred to as "Process 2 (II)" in this document as shown in FIG. 4.

A more hydrophobic compound can be incorporated into the Block B layer by dissolving the compound in the first or second nonprocess solvent as dictated by solubility constraints. The hydrophobic compound can preferentially associate with the nanoparticle when its solubility is reduced by solvent exchange with the second nonprocess solvent or with the reforming solvent. For example, the hydrophobic compound can precipitate when the reforming solvent is introduced in a CIJ mixer. The hydrophobic compound can introduce new functionality to a particle, or be an additional therapeutic agent, or improve encapsulation efficiency of the biologic, or modify release profiles of the encapsulated biologic. In some embodiments, the hydrophobic compound is a lipid.

Final Form Processing

Following precipitation of Block B to form a nanoparticle of structure 301, the nanoparticles may then be processed to a final dosage form by any method known in the art. For example, residual solvent can be removed by distillation, tangential flow filtration, ultrafiltration, or lyophilization. Additional stabilizing excipients may be added to aid in stability or redispersibility.

Particle Degradation and Release

Often, in the course of formulation development, the encapsulation efficiency of a formulation is of interest. This is defined as the fraction of the biologic 101 that remains in the particle core following completion of processing. This metric is indicative of the economics of the process because high losses (low encapsulation efficiency) result in wasted biologic that is not easily recovered for reuse. Ultrafiltration can be used to separate the nanoparticles from unencapsulated biologic and residual nonprocess solvent. For example, an ultrafilter with 100 kDa molecular weight cut-off retains nanoparticles while allowing suitable sized biologics to pass through. The nanoparticles may be concentrated on the ultrafilter, for example, to 10 mg/ml to 15 mg/ml, or 15 mg/ml to 20 mg/ml, or 20 mg/ml to 30 mg/ml, or higher. Additional rinses with a suitable aqueous buffer or with water can be carried out with volumes, for example, from 3 to 5 or 5 to 10 times the concentrated volume. In one embodiment, two additional rinses are employed. Encapsulation efficiency can be determined by measuring with a suitable method the biologic present in the filtrate.

The release profile of the biologic from the nanoparticle core is also central to effectiveness in the desired application. Release can be studied by diluting the final concentrated nanoparticle solution after ultrafiltration into the desired release buffer. The solutions can then be incubated under the required conditions of temperature and agitation. A suitable method to separate nanoparticles from released biologic can be employed at periodic time points to evaluate the released fraction. In one embodiment, ultrafiltration with a 100 kDa molecular weight cut-off is used to separate released biologic from the nanoparticles containing biologic that is still encapsulated. Without being bound by theory, release can occur as a function of degradation of the Block B layer, or by hydrophobic interactions of the encapsulated biologic with Block B, or by ionic interactions with Block C, or by rearrangement of Block B when the glass transition temperature of the block is lower than the release or processing temperature, or by combinations of these mechanisms.

In the examples provided, Process 1 (I) yielded faster release profiles than Process 2 (II). In one example, lysozyme release for Process 1 took about 1 hour to reach 90% while for Process 2, it took about 20-30 hours to reach this level. One skilled in the art would recognize that biologic characteristics will dictate aspects of these release rates as will the media that release is conducted using. These examples indicate that, even with the same solvent combination during reforming (acetone/water), process history dictates release profile characteristics.

The examples provided also illustrate that temperature during the reforming and particle final form processing (e.g. residual nonprocess solvent removal) influences the release profile. Data from these experiments are consistent with a Block B (in this example, PLA) shell that is incomplete, or has cracks or pores. When the processing is conducted at 0-5° C., the release rate is rapid upon warming to the release conditions of 37° C. In contrast, processing under ambient conditions (20° C.) leads to slower release kinetics after warming. These data support a hypothesis of PLA dewetting to form larger pores under release conditions when particles swelling can also occur. This is shown schematically in FIG. 7.

The dewetting is possible under conditions where chain mobility increases, that is, at or above the glass transition temperature ($T_g$). Therefore, processing the nanoparticles after reforming at conditions significantly below the $T_g$ does not allow pore healing. Processing around the $T_g$ in deionized water permits pore healing in an aqueous environment without the presence of salts that lead to swelling of the core. Core swelling can increase the pore size and result in conditions where the pores will not heal.

The relevant $T_g$ value is the $T_g$ of the hydrophobic block under the process conditions (e.g. with water and residual solvent present). This can be measured by standard techniques of the field such as with a differential scanning calorimeter (DSC). Processing (reforming solvent, residual nonprocess solvent removal, etc) at conditions 30° C., 20° C., 10° C., or 5° C. below the $T_g$ does not permit pore healing and leads to faster release than if the reforming and residual nonprocess solvent removal were carried out at the $T_g$ or 5° C., 10° C., 15° C., 20° C., or 30° C. above the $T_g$. Selection of process temperature relative to the $T_g$ of Block B permits facile tuning of release profiles, although one skilled in the art will recognize that characteristics of the biologic encapsulated will influence the absolute magnitude of the release kinetics.

EXAMPLES

Example 1: Nanoparticles Assembled by Process 1 with Triblock Polymer

Biologic (vancomycin, lysozyme) with around 5 mol % labeling by AlexaFluor-488 was dissolved in dimethyl sulfoxide (DMSO) at 12.5 mg/ml. A triblock copolymer of poly(aspartic acid)$_{5kDa}$-b-poly(lactic acid)$_{xkDa}$-b-poly(ethylene glycol)$_{5kDa}$ (PAspA-b-PLA-b-PEG) was dissolved in DMSO at up to 20 mg/ml. The PLA block size was 10 kDa or 20 kDa. In some cases, an A-B-A triblock of PAsp$_{5k}$-PLA$_{10k}$-PAsp$_{5k}$ was used according to the methods of WO 2017/112828 A1 with an initial loading of 50% biologic. A DMSO solution containing 5 vol % water was prepared such that it contained the desired ratio of biologic to polymer (typically 33% biologic by mass for PAspA-PLA-PEG stabilizers) with the mass of the polymer and the biologic totaling 10 mg/ml. An equal volume of an antisolvent stream (nonprocess solvent) of chloroform (or dichloromethane for vancomycin) was prepared. These streams were mixed in an FNP process using a CIJ mixer and collected in a vial containing additional chloroform (dichloromethane for vancomycin) such that the final DMSO content was 10 vol %. This forms a core-shell nanoparticle structure where the biologic comprises the core of the particle with the PAspA and is stabilized by a PLA-PEG corona. A solution of tetraethylene pentamine (TEPA) in chloroform at 5 mg/ml was added dropwise to the nanoparticle solution under rapid stirring to ionically crosslink the PAspA core. The volume added was defined such that 0.7 eq of TEPA was delivered per acid residue on PAspA. The solution was then aged for 30 minutes. At each process step, particle size was measured by dynamic light scattering using a Zetasizer Nano ZS (Malvern, Worcestershire, UK) at 25° C. by diluting each sample ten-fold with the corresponding solvent.

To remove the DMSO, a 150 mM solution of NaCl in water was gently added to the nanoparticle solution such that the aqueous volume was half the chloroform volume. This extraction was carried out on a shaker table for 30 minutes at room temperature. The aqueous layer was separated from the nanoparticle solution. If the A-B-A triblock was used as noted above, a diblock copolymer with Blocks B-C was added at 0.5 times the mass of inverse nanoparticle. The diblock in this example was PLA-PEG as described in WO/2015/200054. An equal volume of acetone was added to the chloroform or DCM. The nanoparticle solution was then solvent swapped into acetone. Typically, this involved a put-and-take distillation by rotovap with 7-8 ml added four times before evaporation to a total mass concentration of 5 mg/ml each time. The solution of nanoparticles in acetone was then mixed in a second FNP step using a CIJ against an equal volume of deionized water. The mixed stream was collected in a vial containing additional deionized water such that the final solution contained 10 vol % acetone.

Residual acetone and unencapsulated biologic were removed by rinsing on a 100 kDa Amicon ultrafilter that had been pre-blocked to prevent non-specific adsorption. The nanoparticle solution was concentrated to around 15-20 mg/ml and rinsed with deionized water twice using a volume that was about 3-4 times the concentrated volume. The flow-through streams were analyzed by fluorescence to determine encapsulation efficiency. The nanoparticles were resuspended in the indicated release buffer and placed on a shaker table at 37° C. for release. Aliquots were taken as indicated and the released fraction was determined by fluorescence measurement on soluble biologic that had been separated from the nanoparticle using a pre-treated 100 kDa ultrafilter. Particle size was characterized by Dynamic Light Scattering (DLS) using a Zetasizer Nano ZS.

The process conditions for each lysozyme formulation are summarized in Table 1. The encapsulation efficiency in the first step was greater than 99% each time. The encapsulation in the final transfer to water was 97-99%. A variety of processing and release conditions were evaluated to characterize the nanoparticle behavior. The conditions as well as the initial release values are summarized in Table 2.

TABLE 1

Summary of nanoparticle composition and formation conditions for Examples 1 & 2

| | Biologic | Polymer | Water (vol % in DMSO) | Loading (%) | Total Conc. In DMSO |
|---|---|---|---|---|---|
| F1 | Lysozyme | PAspA$_5$-b-PLA$_{10}$-b-PEG$_5$ | 5% | 33% | 10 mg/ml |
| F2 | Lysozyme | PAspA$_5$-b-PLA$_{10}$-b-PEG$_5$ | 5% | 33% | 10 mg/ml |
| F3 | Lysozyme | PAspA$_5$-b-PLA$_{10}$-b-PEG$_5$ | 5% | 33% | 10 mg/ml |
| F4 | Lysozyme | PAspA$_5$-b-PLA$_{10}$-b-PAsp$_5$ + PLA$_5$-PEG$_5$ | 5% | 33% | 10 mg/ml |
| F5 | Lysozyme | PAspA$_5$-b-PLA$_{10}$-b-PEG$_5$ | 5% | 33% | 10 mg/ml |
| F6 | Lysozyme | PAspA$_5$-b-PLA$_{10}$-b-PEG$_5$ | 5% | 33% | 10 mg/ml |
| F7 | Lysozyme | PAspA$_5$-b-PLA$_{10}$-b-PEG$_5$ | 5% | 33% | 10 mg/ml |
| F8 | Lysozyme | PAspA$_5$-b-PLA$_{10}$-b-PEG$_5$ | 5% | 33% | 10 mg/ml |

TABLE 2

Summary of processing conditions for nanoparticle formulations from Example 1 & 2

| | Process | Reforming Process Temp (° C.) | Release (° C.) | Initial Fraction Released* |
|---|---|---|---|---|
| F1 | Process 2 | 5° C. | 37° C. | 79% |
| F2 | Process 1 | 5° C. | 37° C. | 64% |
| F3 | Process 2 | 20° C. | 37° C. | 32% |
| F4 | Process 1 | 20° C. | 37° C. | 32% |
| F5 | Process 2 | 20° C. | 5° C. | 22% |
| F6 | Process 2 | 20° C. | 20° C. | 39% |
| F7 | Process 2 | 5° C. | 5° C. | 41% |
| F8 | Process 2 | 5° C. | 20° C. | 75% |

*Fraction released during 20 minutes of sample processing at 20° C. before placement at 37° C. for release.

Figure 5:
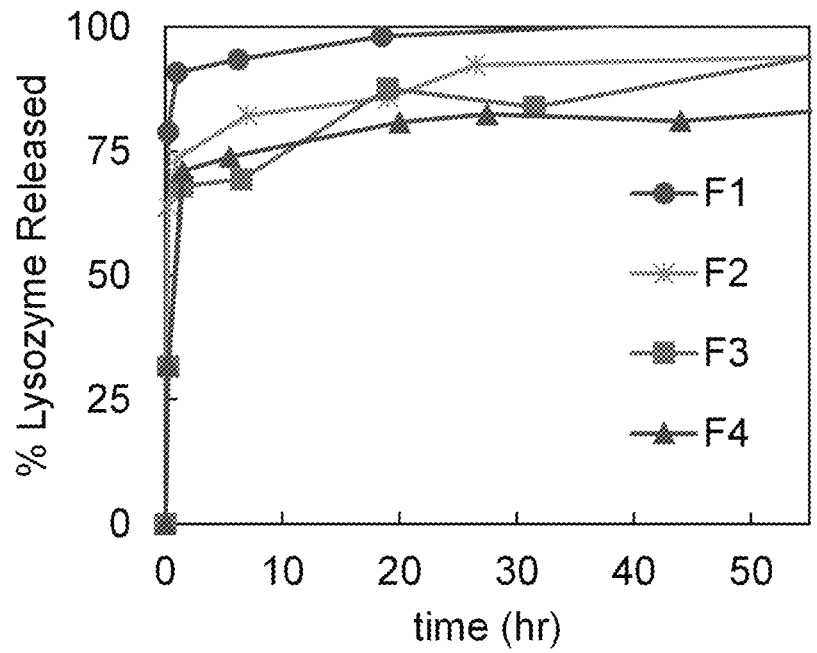
FIG. 5 demonstrates the changes to release profiles as a result of modifications to the formulation. The formulations are summarized in Table 1 and Table 2. F1 is a PAsp$_{5k}$-b-PLA$_{10k}$-PEG$_{5k}$ based NP made in Process 2 with acetone as a nonprocess solvent. The reforming and ultrafiltration was at 5° C. F2 is the same system but made from Process 1 with chloroform as a nonprocess solvent. F3 is the same as F1 but reformed and washed at 20° C. F4 was produced from Process 1 using two block copolymers where the inner polymer was PAsp$_5$-b-PLA$_{10}$-PAsp$_5$ and the outer polymer was PLA-PEG at a 0.5:1 mass ratio of inner stabilizer to outer stabilizer.

The formulation F2 in FIG. 5 was produced according to this example with conditions as noted in Tables 1 & 2. Similarly, F4 was produced with a separate PEG-containing block copolymer to impart stabilization in aqueous environments as described above and in WO/2015/200054. These formulations were compared to those described in Example 2 below.

Example 2: Nanoparticles Assembled by Process 2 with Triblock Polymer

Biologic (vancomycin, lysozyme) with 5 mol % labeling by AlexaFluor-488 was dissolved in dimethyl sulfoxide (DMSO) at 12.5 mg/ml. A triblock copolymer of poly (aspartic acid)$_{5kDa}$-b-poly(lactic acid)$_{xkDa}$-b-poly(ethylene glycol)$_{5kDa}$ (PAspA-b-PLA-b-PEG) was dissolved in DMSO at up to 20 mg/ml. The PLA block size was 10 kDa or 20 kDa. A DMSO solution containing 5 vol % water was prepared such that it contained the desired ratio of lysozyme to polymer (typically up to 33% lysozyme by mass) with the mass of the polymer and the biologic totaling 10 mg/ml. An equal volume of an antisolvent stream (nonprocess solvent) of acetone was prepared. These streams were mixed in an FNP process using a CIJ mixer and collected in a vial containing additional acetone such that the final DMSO content was 10 vol %. This forms a core-shell nanoparticle structure where lysozyme forms the core of the particle with the PAspA and is stabilized by a PLA-PEG brush. A solution of tetraethylene pentamine in chloroform at 5 mg/ml was added dropwise to the nanoparticle solution under rapid stirring to ionically crosslink the PAspA core. The volume added was defined such that 0.7 eq of TEPA was delivered per acid residue from PAspA. The solution was then aged for 30 minutes. Particle size was characterized in each step by DLS.

If indicated, the solution was then cooled to 0-5° C. on wet ice. An equal volume of DI water was also cooled, if indicated, and then mixed with the acetone solution in a reforming step in a CIJ mixer. No additional quench solution was used. The mixed acetone/water solution was then distilled to remove acetone. Conditions were typically 5° C.-20° C. with vacuum applied as appropriate to effect solvent removal.

Residual acetone and unencapsulated lysozyme were removed by rinsing on a 100 kDa Amicon ultrafilter that had been pre-blocked to prevent non-specific adsorption. Temperature was controlled in the centrifugation process to either 5° C. or 20° C. The nanoparticle solution was concentrated to around 15-20 mg/ml and rinsed with deionized water twice using a volume that was about 3-4 times the concentrated volume. The flow-through streams were analyzed by fluorescence to determine encapsulation efficiency. The nanoparticles were resuspended in the indicated release buffer and incubated at 37° C. (unless otherwise indicated) for release. Aliquots were taken as indicated and the released fraction was determined by fluorescence measurement on soluble biologic that had been separated from the nanoparticle using a pre-treated 100 kDa ultrafilter. Particle size was characterized by Dynamic Light Scattering (DLS) using a Zetasizer Nano ZS.

The formulations F1 and F3 were produced according to the methods in this example with parameters as summarized in Tables 1 and 2. Unexpectedly, the lower temperature used in F1 compared to F3 led to faster release kinetics. It would be expected that a lower processing temperature would help maintain a robust PLA (Block B) shell during processing that would then result in slowed release kinetics. Similarly it was unexpected that changing from Process 2 (II) (with acetone as a nonprocess solvent) to Process 1 (I) (with chloroform as a nonprocess solvent) between F2 and F1 would result in a much longer release profile. Without being bound by theory, the use of different antisolvents—even under identical formulation compositions as in F1 and F2—may result in different propensity of the biologic to localize at the Block B interface with the nonprocess solvent. This is a result of the amphiphilic character of many biologics, including lysozyme in this specific case. It was also observed that using a dual diblock copolymer process as described in WO/2015/200054 led to different release profiles than with a single triblock stabilizer even under the identical formulation compositions used in F3/F4. The single triblock stabilizer behavior was similar at early times but release was more rapid at later time periods.

Figure 6:
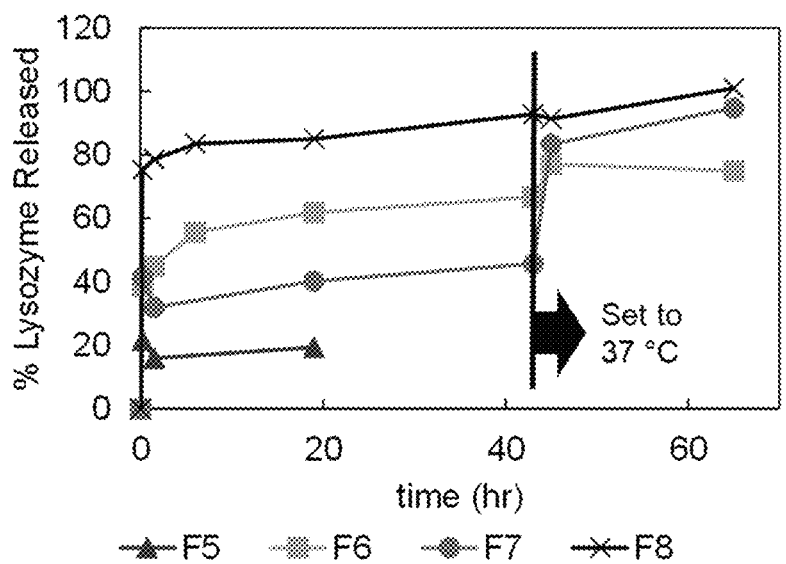
FIG. 6 is the release profile for lysozyme nanoparticles made by Process 2 with acetone as a nonprocess solvent. It demonstrates how reforming and ultrafiltration (processing) temperature and release temperature affect release profiles. Formulation names can be matched with those in Tables 1 & 2. Low temperature lowers the percent that is released rapidly, until the process temperature is raised. Without being bound by theory, raising the temperature results in rapid release consistent with a dewetting process unless all processing was completed at a temperature with higher Block B mobility (in this case, 20° C.). The rapid release, that is consistent with dewetting, is particularly visible following an increase of the release temperature to 37° C.
Figure 7:
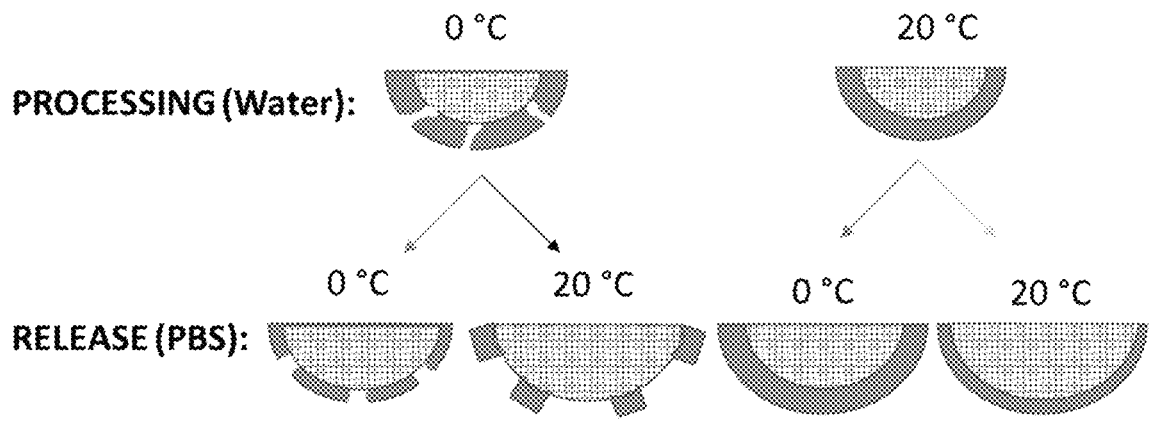
FIG. 7 is a schematic of the theoretical structural differences in the final nanoparticles as a result of different process and release temperatures. The release buffer contains ions that result in core swelling that contribute to dewetting of the hydrophobic polymer under conditions with greater chain mobility.

To better understand the effect of processing temperature, the methods of example 2 were employed with systematically varied temperatures at different process points. Reforming and ultrafiltration temperatures are collectively called processing conditions in Table 2 while the release temperature was also varied. The temperatures had a strong effect on the initial release fraction and the subsequent profile. Release, shown in FIG. 6, at 0-5° C. ("cold" condition) led to the lowest fractions released. However, the lower processing temperature led to the fast release profile when release was carried out at 20° C. ("ambient" condition). Unexpectedly, processing at 20° C. had little effect on encapsulation efficiency and always led to slower release profiles than the corresponding cold processing conditions. Without being bound by theory, we attribute this behavior to a polymer dewetting phenomenon. The PLA block precipitation during reforming may lead to cracks or pores in the shell. When the solution temperature is raised above the Block B glass transition in the presence of residual nonprocess solvent and reforming solvent, there is greater chain mobility. (Analysis of Structural Rearrangements of Poly (lactic acid) in the Presence of Water. Omkar Vyavahare, David Ng, and Shaw Ling Hsu. The Journal of Physical Chemistry B. 2014. 118 (15), 4185-4193) Under these conditions, surface tension can serve as a driving force for dewetting as depicted in FIG. 7. (Direct Measurement of the Critical Pore Size in a Model Membrane. Mark Ilton, Christian DiMaria, and Kari Dalnoki-Veress. Phys. Rev. Lett. 117) The dewetting phenomenon may be more drastic when the nanoparticles are dispersed in release buffer, which promotes swelling of the Block C (PAspA) core due to the presence of ions. Meanwhile, processing in water leads to little swelling and, instead, pore healing rather than dewetting when the processing occurs at sufficient temperature to ensure some chain mobility. Healed pores lead to lower release rates. The drastic effects of dewetting are best seen in the formulation processed cold and then held in release media at 0-5° C. Upon a temperature increase in conditions where core swelling can occur, the remaining encapsulated lysozyme is rapidly released over a few hours because there had been no opportunity for crack healing by processing in water at 20° C. Further, F5 illustrates the strong reduction in burst that occurs from ambient processing followed by cooling to 0-5° C. The lower released fraction versus the sample that had been processed and held for release only at 0-5° C. (F7) is consistent with a pore healing process.

With these insights, it becomes clear that rapid release can be achieved by processing the nanoparticles cold to reduce pore healing as shown in the comparison of F1 & F3 in FIG. 5. Release profiles can be slowed by processing near the solvated glass transition temperature of Block B. One skilled in the art would recognize that use of polymer Block B composition with a different glass transition, solvent dependence, and polymer molecular weight would result in behavior that is different from that observed for PLA (poly(lactic acid) at these conditions, but that it could be recapitulated (reproduced) by processing conditions that mimic the same relative values.

Surprisingly, F1 and F2 exhibited differential release behavior despite being comprised of the same nanoparticle composition. The samples were processed with different solvents in Process 1 and Process 2. Without being limited by theory, the amphiphilic nature of lysozyme can result in differential interactions with the nonprocess solvent. In some cases, this may cause portions of the protein to sit at the Block B interface and change release profiles. Since both processes ultimately end with reforming of Block B in an acetone/water mixture, the differences must be due to the initial particle assembly process in different solvents.

While F3 and F4 were more similar at early timepoints, there is a clear faster release profile for F3 at later timepoints, as seen in FIG. 5. Without being limited by theory, this may be due to the stochastic assembly of the second diblock copolymer for F4, which can help cover cracks and slow release profiles whereas F3 was comprised of a single stabilizer triblock. Taken in sum, these results demonstrate a number of unanticipated levers for tuning release profiles. One would expect that changing the biologic loading would have a measurable effect on release. However, we did not observe any differences on changing loading. However, we did find that the processing solvent choice mattered greatly, as did the manner of stabilizer assembly (triblock or diblock). Importantly, the temperature dependence was counter-intuitive as ambient processing produced slower release profiles than near 0° C. processing.

Example 3: Ovalbumin in a Two-Step Process Using a Triblock Polymer with the pMIVM Ovalbumin (OVA) was dissolved in deionized water at 50 mg/ml. This was diluted into DMSO such that the final composition was 10% water and 5 mg/ml OVA. A triblock copolymer of poly(aspartic acid)$_{5kDa}$-b-poly(lactic acid)$_{10kDa}$-b-poly(ethylene glycol)$_{5kDa}$ (PAspA-b-PLA-b-PEG) was dissolved in DMSO at 15 mg/ml. These solutions were used as input streams to μMIVM (micro multi-inlet vortex mixer) at equal volume. The third inlet stream was THF (tetrahydrofuran) at equal volume while the fourth stream was chloroform at 2.5 times volume. This afforded nanoparticles at 25% loading, with OVA encapsulated in the nanoparticle core. The nanoparticles were stabilized by a PLA-PEG brush layer. Nanoparticle size was characterized by DLS.

A solution of either calcium chloride dihydrate or iron chloride tetrahydrate was prepared in methanol at 38.9 mg/ml or 70.5 mg/ml respectively. A volume of this solution corresponding to a 1:1 charge ratio between the multivalent cation and the negative charge on PAspA was added dropwise while stirring the vial. This solution was aged for 30 min to allow crosslinking of the PAspA residues. A 31 mM solution of ammonia in methanol was prepared. 0.6 eq of ammonia solution was added to the nanoparticle solution dropwise with stirring. The solution was then aged for 30 minutes.

To remove the DMSO, a 150 mM solution of NaCl in water was gently added to the nanoparticle solution such that the aqueous volume was one-third to one-half the chloroform volume. This extraction was carried out on a shaker table for 30 minutes at room temperature. The aqueous layer was separated from the nanoparticle solution. The nanoparticle solution was then solvent swapped into acetone. Typically, this involved a put-and-take distillation by rotovap with 7-8 ml acetone (approximately 1.5 times the initial chloroform volume) added four times with evaporation to a total mass concentration of 5 mg/ml each time. The solution of nanoparticles in acetone was then mixed in a second FNP step using a CIJ against an equal volume of deionized water. The mixed stream was collected in a vial containing additional deionized water such that the final solution contained 10 vol % acetone.

Figure 8:
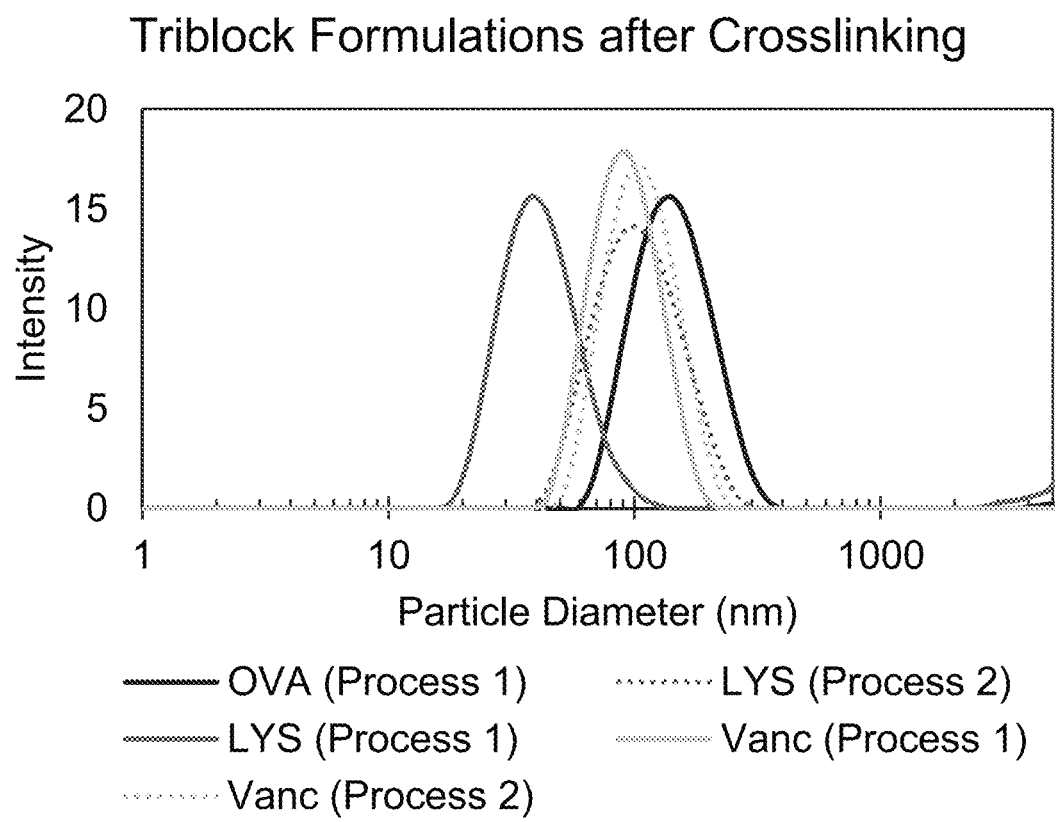
FIG. 8 depicts the triblock copolymer nanoparticle size distribution produced using either Process 1 or Process 2 for ovalbumin (OVA), lysozyme (LYS), and vancomycin (vanc). These three hydrophilic compounds span a range of characteristics that indicate the broad utility of the methods. OVA is plotted in the darkest shade and only for Process 1. Lysozyme is the next darker gray and vancomycin is graphed in the light grey.

Examples 1, 2, and 3 have demonstrated the encapsulation of three different biologics in nanoparticles stabilized by a triblock copolymer. The nanoparticles formed in the first nonprocess solvent step are shown in FIG. 8. The Dynamic Light Scattering (DLS) analysis shows that all formulations have a low polydispersity, with PDI (polydispersity index) values calculated from a cumulants analysis all less than 0.2. Some values are less than 0.1, indicating a relatively monodisperse size population. For lysozyme and vancomycin, both process 1 and process 2 were demonstrated. Importantly, the physical characteristics of these three biologics are quite different. Vancomycin is a short peptide antibiotic; lysozyme is a mid-sized (14.3 kDa) protein with a high surface charge; ovalbumin is a large (43 kDa) protein.

Example 4—Incorporation of Lipid Components into a Triblock Copolymer Formulation It is at times desirable to incorporate hydrophobic compounds into the nanoparticles in addition to the encapsulated biologic. This might be a therapeutic compound, or a lipid component, or an amphiphilic compound with some functional activity. This invention discloses a number of processing schemes that can incorporate compounds fitting this description.

As a demonstration of incorporating a compound that is soluble in the second nonprocess solvent, but assembles upon addition of the reforming solvent, alpha-lecithin can be incorporated into nanoparticles by first dissolving it in the solution after solvent exchange into THF. Rapid mixing with water as a reforming solvent in a CIJ affords nanoparticles.

Lipids such as alpha-lecithin and Lipoid E80 were directly incorporated into the nanoparticles in Process 2 with acetone as a nonprocess solvent. As phosphatidylcholines, the lipids are not soluble in the acetone nonprocess solvent. In some cases, the lipid component will be directly soluble in the more polar process solvent and can be dissolved with the biologic and the polymer components. In other cases, the lipid is not soluble and can be incorporated by using a MIVM to enable more than two inlet streams in the mixing process. Lipoid E80 was incorporated into lysozyme nanoparticles with a composition of 33% triblock copolymer, 33% lipoid, and 33% lysozyme. The lipid was successfully solubilized with 15-20 vol % ethanol in a DMSO polar solvent solution containing the other components.

Figure 9:
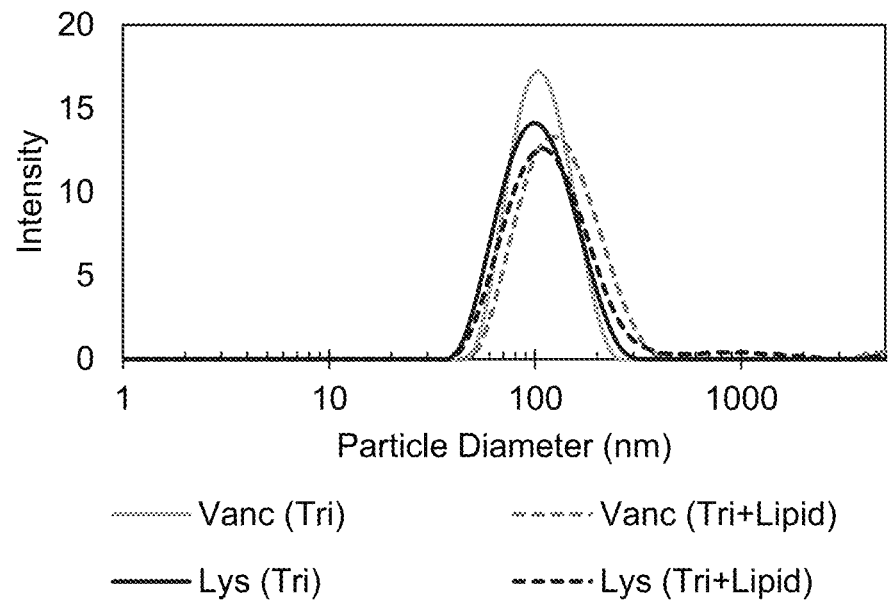
FIG. 9 illustrates the impact of incorporating lipids into nanoparticles by DLS analysis. Both vancomycin and lysozyme were encapsulated. The incorporation of lipids results in in a slight increase in particle size in both cases.
Figure 10:
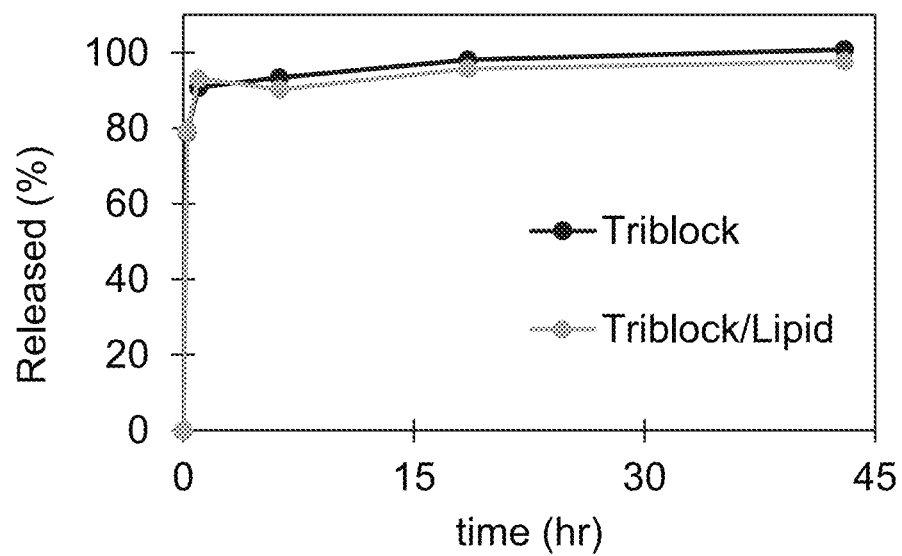
FIG. 10 illustrates that no difference in release profile was observed when a 1:1:1 formulation of lysozyme:triblock:lipid was prepared using acetone as an antisolvent.

FIG. 9 shows the small increase in size by DLS associated with incorporation of the lipid versus a formulation with the same loading of biologic, but consisting of only a triblock stabilizer. FIG. 10 indicates that no difference in release profile was observed under the composition and processing conditions utilized (those of F1 as noted above).

Figure 11:
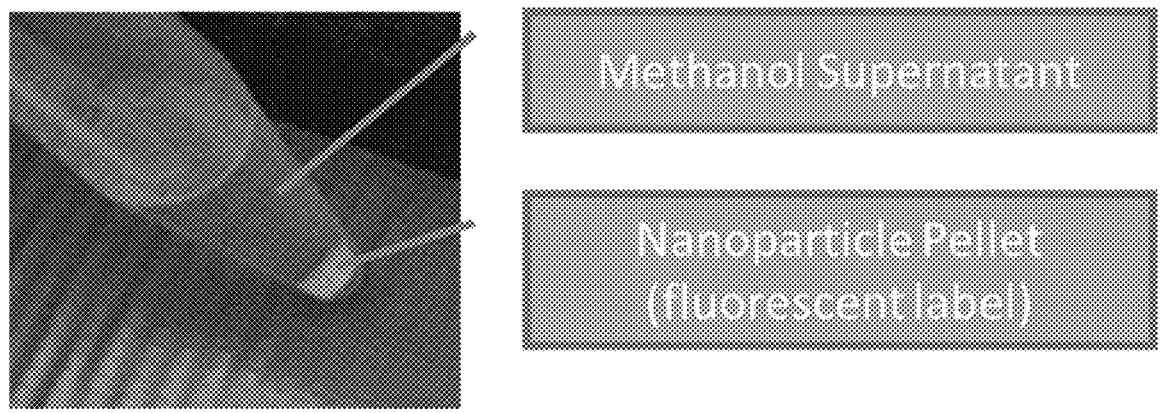
FIG. 11 is a photograph of nanoparticles aggregated together during a solvent exchange into methanol. These were subsequently readily redispersed back into aqueous buffer.

Example 5—Use of Methanol as a Reforming Solvent for a Triblock Copolymer Formulation Vancomycin nanoparticles were prepared as described in Example 1, using a DCM (dichloromethane) antisolvent and 33% biologic loading. The stabilizer was poly(aspartic acid)$_{5kDa}$-b-poly(lactic acid)$_{10kDa}$-b-poly(ethylene glycol)$_{5kDa}$. They were crosslinked with tetraethylene pentamine and extracted as described in Example 1. The particles were concentrated to about 5 mg/ml and 8 ml of methanol was added. This process was repeated a second time to yield a suspension in methanol. The aggregated nanoparticles were pelleted by centrifugation as shown in FIG. 11 and then resuspended in PBS (phosphate buffered saline) to afford a nanoparticle dispersion.

The particle size was measured by DLS following dispersion and was found to have increased from about 90 nm to 135 nm. The sample had a PDI of 0.22. These data suggest that the particles dispersed well in an aqueous environment, with some minor aggregation potentially observed.

Aspects of the Invention

Aspect 1. A method for forming a reformed polymer inverse nanoparticle that encapsulates a water soluble active, comprising:
  dissolving the water soluble active in an amount of a first process solvent to form a first process solution and dissolving a triblock copolymer in an amount of a second process solvent to form a second process solution;
  continuously mixing the first process solution and the second process solution with an amount of a nonprocess solvent to form a first nanoparticle solution comprising a polymer inverse nanoparticle having a core and a shell and a first nanoparticle solvent;
  using the first nanoparticle solution as an intermediate solution, adding a second nonprocess solvent to the first nanoparticle solution to form the intermediate solution, or exchanging the first nanoparticle solvent with the second nonprocess solvent to form the intermediate solution; and
  continuously mixing the intermediate solution with a reforming solvent to form a reformed nanoparticle solution comprising the reformed polymer inverse nanoparticle having a core and a shell,
  wherein the triblock copolymer is a linear [Block A]-[Block B]-[Block C] copolymer,
  wherein Block A is selected from the group consisting of poly(ethylene glycol) and poly(propylene oxide),
  wherein Block B is hydrophobic and is selected from the group consisting of poly(lactic acid), poly(L-lactide), poly(D-lactide), poly(D,L-lactide), poly(glycolic acid), poly(lactic-co-glycolic acid), poly(caprolactone), poly(hydroxyalkanoate), poly(3-hydroxybutyrate), and poly(3-hydroxybutyrate-co-3-hydroxyvalerate),
  wherein Block C is hydrophilic and is selected from the group consisting of poly(aspartic acid) and poly(glutamic acid),
  wherein Block A is soluble in the second process solvent, is soluble in the nonprocess solvent, and is soluble in the reforming solvent,
  wherein Block B is soluble in the nonprocess solvent and is insoluble in the reforming solvent,
  wherein Block C is soluble in the first process solvent, is soluble in the second process solvent, and is insoluble in the nonprocess solvent,
  wherein the water soluble active and Block C are in the core of the polymer inverse nanoparticle and are in the core of the reformed polymer inverse nanoparticle,
  wherein the first process solution is more polar than the nonprocess solvent,
  wherein the second process solution is more polar than the nonprocess solvent,
  wherein the reforming solvent is more polar than the intermediate solution, and
  wherein the amount of the first process solvent, the amount of the second process solvent, and the amount of the nonprocess solvent, when mixed in the absence of the water soluble active or the triblock copolymer, yields a mixture of a single phase or a mixture of which a polar phase is less than 20% of a second phase that is less polar than the polar phase.

Aspect 2. The method of Aspect 1,
  wherein for the polymer inverse nanoparticle Block B and Block A extend away from the core into the first nanoparticle solvent and
  wherein for the reformed polymer inverse nanoparticle Block B is collapsed onto the surface of the core and Block A extends away from the core into the reforming solvent.

Aspect 3. The method of any one of Aspects 1 through 2,
  wherein continuously mixing the intermediate solution with the reforming solvent does not induce precipitation of the reformed polymer inverse nanoparticle and
  wherein the diameter of the reformed polymer inverse nanoparticle is no less than 50% of the diameter of the polymer inverse nanoparticle and is no more than 50% greater than the diameter of the polymer inverse nanoparticle.

Aspect 4. The method of any one of Aspects 1 through 3,
  wherein block A has a molecular weight in the range of from 0.2 kDa to 100 kDa, from 0.5 kDa to 50 kDa, from 1 kDa to 20 kDa, from 2 kDa to 10 kDa, or of about 5 kDa,
  wherein block B has a molecular weight in the range of from 0.5 kDa to 400 kDa, 1 kDa to 200 kDa, from 2 kDa to 100 kDa, from 5 kDa to 40 kDa, from 10 kDa to 20 kDa, of about 10 kDa, or of about 20 kDa, and
  wherein block C has a molecular weight in the range of from 0.2 kDa to 100 kDa, from 0.5 kDa to 50 kDa, from 1 kDa to 20 kDa, from 2 kDa to 10 kDa, or of about 5 kDa.

Aspect 5. The method of any one of Aspects 1 through 4,
  wherein block A is poly(ethylene glycol),
  wherein block B is selected from the group consisting of poly(lactic acid), poly(lactic-co-glycolic acid), and poly(caprolactone), and
  wherein block C is selected from the group consisting of poly(aspartic acid) and poly(glutamic acid).

Aspect 6. The method of any one of Aspects 1 through 5,
  wherein block A has a molecular weight in the range of from 1 kDa to 10 kDa, from 2 kDa to 8 kDa, or of about 5 kDa,
  wherein block B has a molecular weight in the range of from 2 kDa to 100 kDa, 5 kDa to 50 kDa, from 10 kDa to 20 kDa, of about 10 kDa, or of about 20 kDa, and
  wherein block C has a molecular weight in the range of from 1 kDa to 10 kDa, from 2 kDa to 8 kDa, or of about 5 kDa.

Aspect 7. The method of any one of Aspects 1 through 6,
  wherein block A is poly(ethylene glycol) (PEG),
  wherein block B is poly(lactic acid) (PLA), and
  wherein block C is poly(aspartic acid) (PAsp).

Aspect 8. The method of Aspect 7,
  wherein block A has a molecular weight in the range of from 1 kDa to 10 kDa, from 2 kDa to 8 kDa, or of about 5 kDa,
  wherein block B has a molecular weight in the range of from 2 kDa to 100 kDa, 5 kDa to 50 kDa, from 10 kDa to 20 kDa, of about 10 kDa, or of about 20 kDa, and
  wherein block C has a molecular weight in the range of from 1 kDa to 10 kDa, from 2 kDa to 8 kDa, or of about 5 kDa.

Aspect 9. The method of any one of Aspects 1 through 8, wherein the polymer inverse nanoparticle has the core comprising the water soluble active and block C and has the shell comprising block A and block B.

Aspect 10. The method of any one of Aspects 1 through 9, wherein the reformed polymer inverse nanoparticle has the core comprising the water soluble active, block B, and block C and has the shell comprising block A.

Aspect 11. The method of any one of Aspects 1 through 10, further comprising dissolving a lipid in the first process solution or the second process solution.

Aspect 12. The method of any one of Aspects 1 through 11,
  wherein the first process solvent and the second process solvent are the same solvent and together are a single process solvent,
  wherein the water soluble active and the triblock copolymer are dissolved in the single process solvent to form a single process solution,
  wherein the single process solution represents the first process solution and the second process solution, and
  wherein the single process solution is continuously mixed with the amount of the nonprocess solvent to form the first nanoparticle solution comprising a polymer inverse nanoparticle having a core and a shell and a first nanoparticle solvent.

Aspect 13. The method of any one of Aspects 1 through 12,
  wherein a second nonprocess solvent is added to the first nanoparticle solution to form the intermediate solution and
  wherein the second nonprocess solvent is the same solvent as the single process solvent.

Aspect 14. The method of any one of Aspects 1 through 12,
  wherein the first nanoparticle solvent is exchanged with the second nonprocess solvent to form the intermediate solution and
  wherein the first nanoparticle solvent is not miscible with the reforming solvent.

Aspect 15. The method of any one of Aspects 1 through 14,
  wherein the first process solvent is selected from the group consisting of dimethylsulfoxide (DMSO), propanol, ethanol, methanol, water, and combinations, wherein the second process solvent is selected from the group consisting of dimethylsulfoxide (DMSO), propanol, ethanol, methanol, water, and combinations,
wherein the nonprocess solvent is selected from the group consisting of dichloromethane, chloroform, acetone, and tetrahydrofuran (THF),
wherein the second nonprocess solvent is selected from the group consisting of dichloromethane, chloroform, acetone, and tetrahydrofuran (THF), and
wherein the reforming solvent is selected from the group consisting of water, methanol, ethanol, and propanol.

Aspect 16. The method of any one of Aspects 1 through 15, wherein the water soluble active is selected from the group consisting of a linear polypeptide and a cyclic polypeptide.

Aspect 17. The method of any one of Aspects 1 through 16, wherein the first process solvent is completely miscible with the nonprocess solvent and
wherein the second process solvent is completely miscible with the nonprocess solvent.

Aspect 18. The method of any one of Aspects 1 through 17, wherein the continuous mixing is through a flash nanoprecipitation process.

Aspect 19. The method of any one of Aspects 1 through 18, further comprising crosslinking block C.

Aspect 20. The method of any one of Aspects 1 through 18, further comprising ionically crosslinking block C with an organic compound.

Aspect 21. The method of any one of Aspects 1 through 20, further comprising removing the nonprocess solvent from the reformed nanoparticle solution.

Aspect 22. The method of any one of Aspects 1 through 21, further comprising
identifying the desired rate of release of the water soluble active from the reformed polymer inverse nanoparticle and
continuously mixing the intermediate solution with the reforming solvent at a temperature in the range of from 1° C. to 10° C., in the range of from 4° C. to 8° C., or at about 5° C. to achieve a fast rate of release, or
continuously mixing the intermediate solution with the reforming solvent at a temperature in the range of from 15° C. to 35° C., in the range of from 17° C. to 30° C., in the range of from 20° C. to 25° C., or at about 20° C. to achieve a slow rate of release.

Aspect 23. The method of any one of Aspects 12 through 22,
wherein the triblock copolymer is poly(ethylene glycol)-poly(lactic acid)-poly(aspartic acid),
wherein the water soluble active is a polypeptide,
wherein the single process solvent is DMSO or a solution of DMSO and water,
wherein the nonprocess solvent is dichloromethane or chloroform,
wherein following formation of the first nanoparticle solution, the poly(aspartic acid) block is crosslinked through addition of tetraethylene pentamine,
wherein the first nanoparticle solvent is exchanged with the second nonprocess solvent to form the intermediate solution, and
wherein the second nonprocess solvent is acetone.

Aspect 24. The method of any one of Aspects 1 through 23, wherein the reforming solvent is water.

Aspect 25. The method of any one of Aspects 1 through 23, wherein the reforming solvent is methanol.

Aspect 26. The method of any one of Aspects 12 through 23,
wherein the triblock copolymer is poly(ethylene glycol)-poly(lactic acid)-poly(aspartic acid),
wherein the water soluble active is a polypeptide,
wherein the single process solvent comprises DMSO or a solution of DMSO and water,
wherein the nonprocess solvent is acetone,
wherein following formation of the first nanoparticle solution, the poly(aspartic acid) block is crosslinked through addition of tetraethylene pentamine,
wherein the second nonprocess solvent is added to the first nanoparticle solution,
wherein the second nonprocess solvent is acetone, and
wherein the reforming solvent is water.

Aspect 27. The method of any one of Aspects 12 through 26,
wherein a lipid is dissolved into the single process solution and
wherein the single process solvent comprises DMSO, ethanol, and water.

Aspect 28. The method of any one of Aspects 1 through 23,
wherein the triblock copolymer is poly(ethylene glycol)-poly(lactic acid)-poly(aspartic acid),
wherein the water soluble active is a polypeptide,
wherein the first process solvent is a solution of DMSO and water,
wherein the second process solvent is DMSO,
wherein the nonprocess solvent is a solution of tetrahydrofuran (THF) and chloroform,
wherein following formation of the first nanoparticle solution, the poly(aspartic acid) block is crosslinked,
wherein the first nanoparticle solvent is exchanged with a second nonprocess solvent to form the intermediate solution,
wherein the second nonprocess solvent is acetone, and
wherein the reforming solvent is water.

Aspect 29. A method for synthesizing a poly(ethylene glycol)-poly(lactic acid)-poly(aspartic acid) block copolymer (PEG-PLA-PAsp), comprising
providing methoxy-poly(ethylene glycol)-hydroxyl (mPEG-OH),
growing the PLA block from the hydroxyl end of the mPEG-OH through ring opening polymerization to form mPEG-PLA-OH,
converting the mPEG-PLA-OH to form mPEG-PLA-N1-12,
reacting the mPEG-PLA-NH$_2$ with β-Benzyl L-aspartic acid N-carboxyanhydride (Benzyl-Asp-NCA) to form mPEG-PLA-PAsp(Benzyl) (with benzyl-protected PAsp acid groups), and
removing the benzyl protecting groups to form mPEG-PLA-PAsp, Aspect 30. The method of Aspect 29, comprising
forming the mPEG-PLA-OH by adding lactide monomer and a catalyst (for example, 4-(dimethylamino)pyridine (DMAP)) to mPEG-OH in dry chloroform as the solvent and
purifying and recovering the mPEG-PLA-OH through precipitations methanol and isopropanol.

Aspect 31. The method of any one of Aspects 29 through 30, comprising
forming the mPEG-PLA-NH$_2$ by conjugating the acid group of Boc-protected glycine (Boc-Gly) to the hydroxyl end of the mPEG-PLA-OH to form mPEG-PLA-Gly-Boc by using N-(3-dimethylaminopropyl)-N'-ethylcarbodiimide hydrochloride with DMAP as a catalyst in chloroform,
purifying and recovering the mPEG-PLA-Gly-Boc by precipitations in isopropyl alcohol,
removing the Boc group with trifluoroacetic acid in dichloromethane, recovering the mPEG-PLA-NH$_2$ by precipitations in diethyl ether, and optionally desalting to convert the polymer end amine to the free-base form.

Aspect 32. The method of any one of Aspects 29 through 31, comprising removing the benzyl protecting groups by adding concentrated HBr in acetic acid to the mPEG-PLA-PAsp (Benzyl) in chloroform to form mPEG-PLA-PAsp.

Aspect 33. The method of any one of Aspects 29 through 32, further comprising purifying and recovering the mPEG-PLA-PAsp through precipitations in diethyl ether.

The embodiments illustrated and discussed in this specification are intended only to teach those skilled in the art the best way known to the inventors to make and use the invention. Nothing in this specification should be considered as limiting the scope of the present invention. All examples presented are representative and non-limiting. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

The invention claimed is:

1. A method for forming a reformed polymer inverse nanoparticle that encapsulates a water soluble active, comprising:

dissolving the water soluble active in an amount of a first process solvent to form a first process solution and dissolving a triblock copolymer in an amount of a second process solvent to form a second process solution;

continuously mixing the first process solution and the second process solution with an amount of a nonprocess solvent to form a first nanoparticle solution comprising a polymer inverse nanoparticle having a core and a shell and a first nanoparticle solvent;

using the first nanoparticle solution as an intermediate solution, adding a second nonprocess solvent to the first nanoparticle solution to form the intermediate solution, or exchanging the first nanoparticle solvent with the second nonprocess solvent to form the intermediate solution; and continuously mixing the intermediate solution with a reforming solvent to form a reformed nanoparticle solution comprising the reformed polymer inverse nanoparticle having a core and a shell, wherein the triblock copolymer is a linear [Block A]-[Block B]-[Block C] copolymer, wherein Block A is selected from the group consisting of poly(ethylene glycol) and poly(propylene oxide), wherein Block B is hydrophobic and is selected from the group consisting of poly(lactic acid), poly(L-lactide), poly(D-lactide), poly(D,L-lactide), poly(glycolic acid), poly(lactic-co-glycolic acid), poly(caprolactone), poly(hydroxyalkanoate), poly(3-hydroxybutyrate), and poly(3-hydroxybutyrate-co-3-hydroxyvalerate), wherein Block C is hydrophilic and is selected from the group consisting of poly(aspartic acid) and poly(glutamic acid), wherein Block A is soluble in the second process solvent, is soluble in the nonprocess solvent, and is soluble in the reforming solvent, wherein Block B is soluble in the nonprocess solvent and is insoluble in the reforming solvent, wherein Block C is soluble in the first process solvent, is soluble in the second process solvent, and is insoluble in the nonprocess solvent, wherein the water soluble active and Block C are in the core of the polymer inverse nanoparticle and are in the core of the reformed polymer inverse nanoparticle, wherein Block C is not in the shell of the reformed polymer inverse nanoparticle, wherein Block C does not extend away from the core into the reforming solvent, wherein the first process solvent is more polar than the nonprocess solvent, wherein the second process solvent is more polar than the nonprocess solvent, wherein an intermediate solvent is the intermediate solution without the polymer inverse nanoparticle, wherein the reforming solvent is more polar than the intermediate solvent, wherein the amount of the first process solvent, the amount of the second process solvent, and the amount of the nonprocess solvent, when mixed in the absence of the water soluble active or the triblock copolymer, yields a mixture of a single phase or a mixture of which a polar phase is less than 20% of a second phase that is less polar than the polar phase, wherein the first process solvent is selected from the group consisting of dimethylsulfoxide (DMSO), propanol, ethanol, methanol, water, and a combination, wherein the second process solvent is selected from the group consisting of dimethylsulfoxide (DMSO), propanol, ethanol, methanol, water, and a combination, wherein the nonprocess solvent is selected from the group consisting of dichloromethane, chloroform, acetone, tetrahydrofuran (THF), and a combination, wherein the second nonprocess solvent is selected from dichloromethane, chloroform, acetone, tetrahydrofuran (THF), and a combination, wherein the reforming solvent is selected from water, methanol, ethanol, propanol, and a combination.

2. The method of claim 1, wherein for the polymer inverse nanoparticle Block B and Block A extend away from the core into the first nanoparticle solvent and wherein for the reformed polymer inverse nanoparticle Block B is collapsed onto the surface of the core and Block A extends away from the core into the reforming solvent.

3. The method of claim 1, wherein continuously mixing the intermediate solution with the reforming solvent does not induce precipitation of the reformed polymer inverse nanoparticle and wherein the diameter of the reformed polymer inverse nanoparticle is no less than 50% of the diameter of the polymer inverse nanoparticle and is no more than 50% greater than the diameter of the polymer inverse nanoparticle.

4. The method of claim 1, wherein block A has a molecular weight in the range of from 0.2 kDa to 100 kDa, from 0.5 kDa to 50 kDa, from 1 kDa to 20 kDa, from 2 kDa to 10 kDa, or of about 5 kDa, wherein block B has a molecular weight in the range of from 0.5 kDa to 400 kDa, 1 kDa to 200 kDa, from 2 kDa to 100 kDa, from 5 kDa to 40 kDa, from 10 kDa to 20 kDa, of about 10 kDa, or of about 20 kDa, and wherein block C has a molecular weight in the range of from 0.2 kDa to 100 kDa, from 0.5 kDa to 50 kDa, from 1 kDa to 20 kDa, from 2 kDa to 10 kDa, or of about 5 kDa.

5. The method of claim 1,
wherein block A is poly(ethylene glycol),
wherein block B is selected from the group consisting of poly(lactic acid), poly(lactic-co-glycolic acid), and poly(caprolactone), and
wherein block C is selected from the group consisting of poly(aspartic acid) and poly(glutamic acid).

6. The method of claim 1,
wherein block A has a molecular weight in the range of from 1 kDa to 10 kDa, from 2 kDa to 8 kDa, or of about 5 kDa,
wherein block B has a molecular weight in the range of from 2 kDa to 100 kDa, 5 kDa to 50 kDa, from 10 kDa to 20 kDa, of about 10 kDa, or of about 20 kDa, and
wherein block C has a molecular weight in the range of from 1 kDa to 10 kDa, from 2 kDa to 8 kDa, or of about 5 kDa.

7. The method of claim 1,
wherein block A is poly(ethylene glycol) (PEG),
wherein block B is poly(lactic acid) (PLA), and
wherein block C is poly(aspartic acid) (PAsp).

8. The method of claim 7,
wherein block A has a molecular weight in the range of from 1 kDa to 10 kDa, from 2 kDa to 8 kDa, or of about 5 kDa,
wherein block B has a molecular weight in the range of from 2 kDa to 100 kDa, 5 kDa to 50 kDa, from 10 kDa to 20 kDa, of about 10 kDa, or of about 20 kDa, and
wherein block C has a molecular weight in the range of from 1 kDa to 10 kDa, from 2 kDa to 8 kDa, or of about 5 kDa.

9. The method of claim 1, wherein the polymer inverse nanoparticle has the core comprising the water soluble active and block C and has the shell comprising block A and block B.

10. The method of claim 1, wherein the reformed polymer inverse nanoparticle has the core comprising the water soluble active, block B, and block C and has the shell comprising block A.

11. The method of claim 1, further comprising dissolving a lipid in the first process solution or the second process solution.

12. The method of claim 1,
wherein the first process solvent and the second process solvent are the same solvent and together are a single process solvent,
wherein the water soluble active and the triblock copolymer are dissolved in the single process solvent to form a single process solution,
wherein the single process solution represents the first process solution and the second process solution, and
wherein the single process solution is continuously mixed with the amount of the nonprocess solvent to form the first nanoparticle solution comprising a polymer inverse nanoparticle having a core and a shell and a first nanoparticle solvent.

13. The method of claim 12,
wherein the second nonprocess solvent is the same solvent as the single process solvent.

14. The method of claim 1,
wherein the first nanoparticle solvent is exchanged with the second nonprocess solvent to form the intermediate solution and wherein the first nanoparticle solvent is not miscible with the reforming solvent.

15. The method of claim 1,
wherein the first process solvent is selected from the group consisting of dimethylsulfoxide (DMSO), propanol, ethanol, methanol, water, and combinations,
wherein the second process solvent is selected from the group consisting of dimethylsulfoxide (DMSO), propanol, ethanol, methanol, water, and combinations,
wherein the nonprocess solvent is selected from the group consisting of dichloromethane, chloroform, acetone, and tetrahydrofuran (THF),
wherein the second nonprocess solvent is selected from the group consisting of dichloromethane, chloroform, acetone, and tetrahydrofuran (THF), and
wherein the reforming solvent is selected from the group consisting of water, methanol, ethanol, and propanol.

16. The method of claim 1, wherein the water soluble active is selected from the group consisting of a linear polypeptide and a cyclic polypeptide.

17. The method of claim 1, wherein the first process solvent is completely miscible with the nonprocess solvent and wherein the second process solvent is completely miscible with the nonprocess solvent.

18. The method of claim 1, wherein the continuous mixing is through a flash nanoprecipitation process.

19. The method of claim 1, further comprising crosslinking block C.

20. The method of claim 1, further comprising ionically crosslinking block C with an organic compound.

21. The method of claim 1, further comprising removing the nonprocess solvent from the reformed nanoparticle solution.

22. The method of claim 1, further comprising
identifying the desired rate of release of the water soluble active from the reformed polymer inverse nanoparticle and
continuously mixing the intermediate solution with the reforming solvent at a temperature in the range of from 1° C. to 10° C., in the range of from 4° C. to 8° C., or at about 5° C. to achieve a fast rate of release, or
continuously mixing the intermediate solution with the reforming solvent at a temperature in the range of from 15° C. to 35° C., in the range of from 17° C. to 30° C., in the range of from 20° C. to 25° C., or at about 20° C. to achieve a slow rate of release.

23. The method of claim 12,
wherein the triblock copolymer is poly(ethylene glycol)-poly(lactic acid)-poly(aspartic acid),
wherein the water soluble active is a polypeptide,
wherein the single process solvent is DMSO or a solution of DMSO and water,
wherein the nonprocess solvent is dichloromethane or chloroform,
wherein following formation of the first nanoparticle solution, the poly(aspartic acid) block is crosslinked through addition of tetraethylene pentamine,
wherein the first nanoparticle solvent is exchanged with the second nonprocess solvent to form the intermediate solution, and
wherein the second nonprocess solvent is acetone.

24. The method of claim 1, wherein the reforming solvent is water.

25. The method of claim 1, wherein the reforming solvent is methanol.

26. The method of claim 12,
wherein the triblock copolymer is poly(ethylene glycol)-poly(lactic acid)-poly(aspartic acid),
wherein the water soluble active is a polypeptide,
wherein the single process solvent comprises DMSO or a solution of DMSO and water,
wherein the nonprocess solvent is acetone,
wherein following formation of the first nanoparticle solution, the poly(aspartic acid) block is crosslinked through addition of tetraethylene pentamine,
wherein the second nonprocess solvent is added to the first nanoparticle solution,
wherein the second nonprocess solvent is acetone, and
wherein the reforming solvent is water.

27. The method of claim 12,
wherein a lipid is dissolved into the single process solution and
wherein the single process solvent comprises DMSO, ethanol, and water.

28. The method of claim 1,
wherein the triblock copolymer is poly(ethylene glycol)-poly(lactic acid)-poly(aspartic acid),
wherein the water soluble active is a polypeptide,
wherein the first process solvent is a solution of DMSO and water,
wherein the second process solvent is DMSO,
wherein the nonprocess solvent is a solution of tetrahydrofuran (THF) and chloroform,
wherein following formation of the first nanoparticle solution, the poly(aspartic acid) block is crosslinked,
wherein the first nanoparticle solvent is exchanged with the second nonprocess solvent to form the intermediate solution,
wherein the second nonprocess solvent is acetone, and
wherein the reforming solvent is water.

29. The method of claim 1, wherein Block A is poly(propylene oxide).

30. The method of claim 1, wherein Block B is poly(3-hydroxybutyrate-co-3-hydroxyvalerate).

* * * * *